US012611474B2

(12) United States Patent
Liu et al.

(10) Patent No.: US 12,611,474 B2
(45) Date of Patent: Apr. 28, 2026

(54) GLIDING ARC AND DIELECTRIC BARRIER DISCHARGE COMBINED DISCHARGE PLASMA DISINFECTION DEVICE AND METHOD

(71) Applicant: XI'AN JIAOTONG UNIVERSITY, Xi'an (CN)

(72) Inventors: Dingxin Liu, Xi'an (CN); Zifeng Wang, Xi'an (CN); Linbo Liu, Xi'an (CN); Jinkun Chen, Xi'an (CN); Mengying Zhu, Xi'an (CN); Li Guo, Xi'an (CN); Xiaohua Wang, Xi'an (CN); Mingzhe Rong, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 1143 days.

(21) Appl. No.: 17/575,230

(22) Filed: Jan. 13, 2022

(65) Prior Publication Data

US 2022/0265879 A1     Aug. 25, 2022

(30) Foreign Application Priority Data

Feb. 24, 2021     (CN) ........................ 202110209052.X

(51) Int. Cl.
| | |
|---|---|
| *H05H 1/48* | (2006.01) |
| *A61L 2/14* | (2006.01) |
| *H05H 1/24* | (2006.01) |

(52) U.S. Cl.
CPC ............. *A61L 2/14* (2013.01); *H05H 1/2406* (2013.01); *H05H 1/482* (2021.05); *A61L 2202/11* (2013.01); *A61L 2202/14* (2013.01)

(58) Field of Classification Search
CPC ........................ A61L 2202/122; H05H 1/2406
See application file for complete search history.

(56) References Cited

U.S. PATENT DOCUMENTS

2004/0262146 A1 * 12/2004 Platt, Jr. .................... A61L 2/24
422/23

FOREIGN PATENT DOCUMENTS

| | | | | |
|---|---|---|---|---|
| JP | 2019136543 A | * | 8/2019 | ............... A61L 2/07 |
| KR | 20070029682 A | * | 3/2007 | ............ H01J 37/244 |

(Continued)

OTHER PUBLICATIONS

KR_20070029682_A_translation (Year: 2007).*

(Continued)

*Primary Examiner* — Kevin Joyner
*Assistant Examiner* — Changru Chen

(57)     ABSTRACT

The present disclosure discloses a discharge plasma disinfection device and method thereof. In the disinfection device, a gliding arc electrode pair generates the RNS-dominated reactive gas under the excitation of a gliding arc high-voltage power supply; and a dielectric barrier discharge electrode pair generates the ROS-dominated reactive gas under the excitation of a dielectric barrier discharge high-voltage power supply. These two reactive gases are introduced into a mixing chamber in a specific ratio and are subjected to an effective mixing reaction through an internal recycle system to obtain RNS/ROS mixed reactive gas in which reactive nitrogen species and reactive oxygen species coexist. The RNS/ROS mixed reactive gas may be directly configured to perform disinfection, and may also be configured to process an aqueous solution and then perform disinfection by the processed plasma-activated water.

6 Claims, 12 Drawing Sheets

(56)     References Cited

FOREIGN PATENT DOCUMENTS

| KR | 20120124152 | A | * | 11/2012 | ............... | A61L 2/20 |
| KR | 101682885 | B1 | * | 12/2016 | ............... | A23B 4/16 |
| WO | WO-2019084203 | A1 | * | 5/2019 | ........... | A61L 2/0082 |
| WO | WO-2020152685 | A1 | * | 7/2020 | ............. | A23B 7/144 |

OTHER PUBLICATIONS

KR_101682885_B1_translation (Year: 2016).*
JP_2019136543_A_translation (Year: 2019).*
KR_20120124152_A_translation (Year: 2012).*

* cited by examiner

GLIDING ARC AND DIELECTRIC BARRIER DISCHARGE COMBINED DISCHARGE PLASMA DISINFECTION DEVICE AND METHOD

CROSS-REFERENCE TO RELATED APPLICATION

This application claims priority from the Chinese patent application 202110209052.X filed Feb. 24, 2021, the content of which is incorporated herein in the entirety by reference.

TECHNICAL FIELD

The disclosure belongs to the field of plasma disinfection, and particularly relates to a discharge plasma disinfection device and method that combines a nitrogen oxide mode and an ozone mode.

BACKGROUND

Pathogenic microorganisms widely exist in our daily life, and we are always in contact with various microorganisms, so pathogenic microorganism infection has become an important factor threatening human health and safety, and people also have a huge demand for efficient environmental disinfection and food preservation methods. How to realize anti-infection in vivo and environmental disinfection safely and efficiently has always been a problem we explore. At present, the most commonly used anti-infection method is antibiotic therapy, and the most commonly used environmental disinfection method is chemical disinfectants. However, the antibiotic drug has the problems of drug resistance and double infection; and the traditional chemical disinfectant is usually difficult to degrade and pollute the environment. Therefore, it is very important to research and develop a microbial killing method that is safe to the human body, free of toxic or side effects, and environmentally friendly.

In recent years, the atmospheric pressure cold plasma technology has been widely researched in the fields of environmental protection, biomedicine, material modification, and chemical production, and it has been proved that plasma sterilization has a broad application prospect. Plasma gaseous reactive species generated by discharge generate aqueous reactive species such as $H_2O_2$, ONOOH, NO, and OH in water through a series of dissolution or chemical reactions. These substances have a small dosage which is generally less than an order of magnitude of 1 mM, and can have a good killing effect on many bacteria and viruses. The plasma with a controlled dosage may avoid damage to human cells while killing bacteria. Compared with the traditional disinfection mode, plasma disinfection has the advantages of high sterilization efficiency, insusceptibility to generate drug resistance, no toxic or side effects, no environmental pollution and the like.

The usual plasma disinfection mode includes nitrogen oxide mode discharge and ozone mode discharge. The plasma-activated water generated from the reaction of the RNS/ROS mixed reactive gas and the aqueous solution can effectively remove organic pollutants and pathogenic microorganisms from water. The ozone mode mainly generates ozone, and the nitrogen oxide mode mainly generates low-valent nitrogen oxides such as nitric oxide and nitrogen dioxide. The two modes are very sensitive to power density and gas temperature. For example, the two modes are often converted at a gas temperature between 40 DEG C. and 60 DEG C.

The main problem of the ozone mode for disinfection is that the ozone has low solubility. Although high-concentration ozone can be generated in the air, the ozone in a liquid solution has low concentration and low permeability to a cell membrane, which limits the sterilization ability. The main problem of the nitrogen oxide mode for disinfection is that the low sterilization effect of NO and $NO_2$. It is difficult to achieve high sterilization efficiency by using the plasma in one of the modes alone.

A "coexistence state" mode of reactive oxygen species and reactive nitrogen species may be generated under the specific condition. If a transition state of ozone mode and nitrogen oxide mode is adopted for discharging, the solubility of the mixed reactive gas in water will be greatly improved, and a large amount of high-valence nitrogen oxides that play a key role in sterilization will be produced, such as $NO_3$ and $N_2O_5$. However, the discharge in this mode is the discharge in the coexistence transition state mode, and the transition state is very sensitive to gas temperature, gas flow speed, and power density. In other words, the discharge in this mode is easily converted into nitrogen oxide mode or ozone mode, and maintaining the stability of the discharge in this mode has extremely high requirements on power density control of the device and control of discharge temperature. Hence, the cost of plasma disinfection commercial preparation is greatly increased, the stability of the device is poor and the yield of aqueous reactive species is not high.

The above information disclosed in the background section is only used to enhance the understanding of the background of the present disclosure, so the information may include information which does not constitute the prior art well-known to a person of ordinary skill in the art in China.

SUMMARY

In view of the problems in the prior art, the present disclosure provides a discharge plasma disinfection device and method combining the nitrogen oxide mode and the ozone mode, which mixes the plasma reactive gas generated by the combination of the nitrogen oxide mode and the ozone mode, the use of mixed reactive gases for various methods of disinfection treatment will not produce side effects, is friendly to human tissues and the environment, and has a good disinfection effect. The problems of low solubility and permeability of the reactive oxygen species, low oxidability of the reactive nitrogen species and low transition state stability are solved, and the defect that the plasma reactive gas generated by a single discharge form has low solubility and weak reactivity is overcome. By mixing a large amount of high-valence $NO_3$ and $N_2O_5$, it reacts quickly in water and cytoplasm to produce ONOOH and $O_2NOOH$. These two kinds of species have strong permeability to cell membranes and a strong ability to inactivate pathogenic microorganisms, thereby realizing high-efficiency disinfection and sterilization applications.

In view of the problems in the prior art, the present disclosure also provides a dielectric barrier discharge and gliding arc combined discharge plasma disinfection device and method. The RNS-dominated reactive gas and ROS-dominated reactive gas generated by a combination of the gliding arc and the dielectric barrier discharge are mixed to realize the coexistence of reactive nitrogen species (RNS) and reactive oxygen species (ROS). Disinfection treatment is performed in various ways by using RNS/ROS mixed reactive gas, so the side effects are avoided, it is friendly to human tissue and environment, a good disinfection effect is achieved, the problems of low solubility and permeability of the reactive oxygen species, low oxidability of the reactive nitrogen species and low transition state stability are solved, and the defect that the plasma reactive gas generated by a single discharge form has low solubility and weak reactivity is overcome. The concentration, utilization rate, and the dissolution rate in the aqueous solution of the RNS/ROS mixed reactive gas in which the reactive nitrogen species and the reactive oxygen species coexist are increased, so that efficient disinfection application is realized. In the present disclosure, ROS refers to plasma-induced biochemically reactive gaseous or aqueous substances generated by air discharge containing only oxygen element, such as ozone, oxygen atom, singlet oxygen, superoxide anion; RNS refers to plasma-induced biochemically reactive gaseous or aqueous substances generated by air discharge containing nitrogen element, such as nitric oxide, nitrogen dioxide, dinitrogen pentoxide, nitrate, nitrite, peroxynitrite.

The present disclosure provides a discharge plasma disinfection device, comprising:

a first A electrode and a first B electrode, used for:
generating a first plasma gas under a first voltage, wherein the first plasma gas is mainly produced by nitrogen oxide;

a second A electrode and a second B electrode, used for:
generating a second plasma gas under a second voltage, wherein the second plasma gas is mainly produced by ozone; and a reactive gas mixing unit, configured to mix the first plasma gas and the second plasma gas to form a mixed reactive gas;

wherein the mixed reactive gas can be directly used for disinfection and sterilization, or the aqueous solution is processed first, and then the plasma-activated water is used for disinfection and sterilization.

Preferably, wherein the first plasma gas and the second plasma gas are mixed as follows:

the volume of the ozone reactive gas: the volume of the nitrogen oxide reactive gas $$\geq \frac{0.556b + 0.051c}{0.328a},$$

wherein a is an absorption value of a Fourier infrared absorption spectrum of the second plasma gas at the position with a wave-number of 1055 cm$^{-1}$, b being an absorption value of a Fourier infrared absorption spectrum of the first plasma gas at the position of a wave-number of 1630 cm$^{-1}$, and c being an absorption value of a Fourier infrared absorption spectrum of the first plasma gas at the position of a wave-number of 1900 cm$^{-1}$.

More preferably, wherein the discharge plasma disinfection device further comprises:

a first high-voltage power, configured to provide a first voltage;

a first plasma source, connected to the first high-voltage power supply, the first plasma source comprising;

a first plasma chamber, provided with a first air inlet and a first air outlet, the first air outlet communicating with a first controllable flow gas pump;

a first A electrode, connected to the first high-voltage power supply; and

a first B electrode, connected to the first high-voltage power supply;

wherein the first A electrode and the first B electrode generate a first plasma gas in the first plasma chamber under a first voltage, and the first plasma gas is dominated by nitrogen oxides.

More preferably, wherein the discharge plasma disinfection device further comprises:

a second high-voltage power, configured to provide a second voltage;

a second plasma source, connected to the second high-voltage power supply, the second plasma source comprising;

a second plasma chamber, provided with a second air inlet and a second air outlet, the second air outlet communicating with a second controllable flow gas pump;

a second A electrode, connected to the second high-voltage power supply;

a second B electrode, connected to the second high-voltage power supply;

an insulating dielectric plate, set between the second A electrode and the second B electrode;

the second A electrode and the second B electrode generate a second plasma gas in the second plasma chamber under a second voltage, and the second plasma gas is dominated by ozone;

a reactive gas mixing unit, comprising;

an inlet, connected to the first controllable flow air pump and the second controllable flow air pump; and a reactive gas mixing chamber, connected to the inlet to mix the first plasma gas and the second plasma gas to form the mixed reactive gas.

More preferably, wherein the first high-voltage power supply includes a sinusoidal power supply, a radio frequency power supply, or a direct current power supply, and the voltage of the first high-voltage power supply is more than 10 kV and the output power is more than 200 W, and the voltage of the second high-voltage power supply is more than 5 kV and the output power is more than 8 W.

More preferably, wherein the disinfection device further comprises a gas spray disinfection unit and/or a gas filling disinfection unit based on the mixed reactive gas, both of which are connected to the outlet of the reactive gas mixing unit.

More preferably, wherein the reactive gas mixing unit further comprises:

a heater, configured to heat the mixed reactive gas in a reactive gas mixing chamber and control the temperature of the reactive gas mixing chamber to be 30-50 DEG C.; and an ultraviolet lamp, configured to irradiate the mixed reactive gas.

More preferably, wherein the first air inlet and the second air inlet are connected to an air supplement valve, and the air supplement valve is a one-way valve without opening air pressure, and its outlet is connected to the first air inlet and the second air inlet.

More preferably, wherein the first controllable flow air pump and the second controllable flow air pump are connected to the inlet via a check valve.

The present disclosure also provides a method for disinfection using the disinfection device, comprising the following steps:

utilizing the first high-voltage power supply to provide the first voltage, the first plasma source generates the first plasma gas, and the first plasma gas takes nitrogen oxide as the main product;

utilizing a second high-voltage power supply to provide a second voltage, the second plasma source generates a second plasma gas, and the second plasma gas uses ozone as a dominant product;

enabling the first gas outlet to export a first predetermined amount of first plasma gas via a first controllable flow gas pump;

enabling the second gas outlet to export a second predetermined amount of second plasma gas via a second controllable flow gas pump;

wherein the first plasma gas and the second plasma gas are formed into a mixed reactive gas in the reactive gas mixing chamber according to the mixing ratio, wherein the mixing ratio is:

the volume of the ozone reactive gas: the volume of the nitrogen oxide reactive gas $$\geq \frac{0.556b + 0.051c}{0.328a},$$

wherein a is an absorption value of a Fourier infrared absorption spectrum of the second plasma gas at the position with a wave-number of 1055 cm$^{-1}$, b being an absorption value of a Fourier infrared absorption spectrum of the first plasma gas at the position of a wave-number of 1630 cm$^{-1}$, and c being an absorption value of a Fourier infrared absorption spectrum of the first plasma gas at the position of a wave-number of 1900 cm$^{-1}$.

The present disclosure also provides a discharge plasma disinfection device, comprising:

a gliding arc electrode pair, configured to generate the RNS-dominated reactive gas under the excitation of a gliding arc high-voltage power supply;

a dielectric barrier discharge electrode pair, configured to generate the ROS-dominated reactive gas under the excitation of a dielectric barrier discharge high-voltage power supply;

an internal recycle system unit, configured to reconnect the unused RNS/ROS mixed reactive gas to a gas input end of the gliding arc electrode pair and a gas input end of the dielectric barrier discharge electrode pair; and a reactive gas mixing unit, configured to mix the RNS-dominated reactive gas and the ROS-dominated reactive gas to form the RNS/ROS mixed reactive gas;

wherein the RNS/ROS mixed reactive gas is directly configured to perform disinfection, or is configured to process an aqueous solution and then perform disinfection by using plasma-activated water.

More preferably, wherein the disinfection device further comprises:

a gliding arc high-voltage power supply;

a gliding arc plasma source, comprising:

a gliding arc electrode pair, connected to the gliding arc high-voltage power supply and generating the RNS-dominated reactive gas under the excitation of the gliding arc high-voltage power supply;

a gliding arc controllable flow gas pump;

a dielectric barrier discharge high-voltage power supply;

a dielectric barrier discharge plasma source, comprising:

a dielectric barrier discharge electrode pair, connected to the dielectric barrier discharge high-voltage power supply and generating the ROS-dominated reactive gas under the excitation of the dielectric barrier discharge high-voltage power supply;

and a dielectric barrier discharge controllable flow gas pump.

More preferably, wherein the disinfection device further comprises:

a reactive gas mixing unit, comprising:

an inlet, connected to a gliding arc controllable flow gas pump and a dielectric barrier discharge controllable flow gas pump;

a reactive gas mixing chamber, connected to the inlet to mix the RNS-dominated reactive gas and the ROS-dominated reactive gas to form the RNS/ROS mixed reactive gas; and an internal recycle system unit, connecting the unused RNS/ROS mixed reactive gas to a gas inlet end of the gliding arc plasma source and a gas inlet end of the dielectric barrier discharge plasma source.

More preferably, wherein the gliding arc high-voltage power supply comprises a sine power supply or a direct-current power supply, the gliding arc high-voltage power supply has a voltage of more than 5 kV and output power of more than 40 W, and the dielectric barrier discharge high-voltage power supply has a voltage of more than 5 kV and output power of more than 8 W.

More preferably, wherein the disinfection device further comprises:

a gas injection disinfection unit and/or a gas filling disinfection unit based on the RNS/ROS mixed reactive gas, which is connected to an outlet of the reactive gas mixing unit.

More preferably, wherein the mixing ratio of the RNS-dominated reactive gas and the ROS-dominated reactive gas entering the reactive gas mixing unit is as follows:

the volume ratio of the RNS-dominated reactive gas to the ROS-dominated reactive gas is less than or equal to $$\frac{0.328a}{0.556b + 0.051c},$$

a being an absorption value of a Fourier infrared absorption spectrum of the ROS-dominated reactive gas at the position with a wave-number of 1055 cm$^{-1}$, b being an absorption value of a Fourier infrared absorption spectrum of the RNS-dominated reactive gas at the position of a wave-number of 1630 cm$^{-1}$, and c being an absorption value of a Fourier infrared absorption spectrum of the RNS-dominated reactive gas at the position of a wave-number of 1900 cm$^{-1}$.

More preferably, wherein the reactive gas mixing unit further comprises:

a heater, configured to heat the RNS/ROS mixed reactive gas in a reactive gas mixing chamber and control the temperature of the reactive gas mixing chamber to be 30-50 DEG C.; and an ultraviolet lamp, configured to irradiate the RNS/ROS mixed reactive gas.

More preferably, wherein a gas inlet of the gliding arc plasma source and a gas inlet of the dielectric barrier discharge plasma source are connected to a gas supplementing valve, the gas supplementing valve is a one-way valve without an open gas pressure, and an outlet of the gas supplementing valve is connected to the gas inlet of the gliding arc plasma source and the gas inlet of the dielectric barrier discharge plasma source.

More preferably, wherein the gliding arc controllable flow gas pump and the dielectric barrier discharge controllable flow gas pump are connected to the inlet through a check one-way valve.

The present disclosure also provides a method for performing disinfection by using the disinfection device, comprising the following steps:

provided a discharge voltage of a gliding arc plasma source by using a gliding arc high-voltage power supply, wherein the gliding arc plasma source generates the RNS-dominated reactive gas;

providing a discharge voltage of a dielectric barrier discharge plasma source by using a dielectric barrier discharge high-voltage power supply, wherein the dielectric barrier discharge plasma source generates the ROS-dominated reactive gas;

enabling the gliding arc gas outlet to export a predetermined amount of the RNS-dominated reactive gas through the gliding arc controllable flow gas pump;

enabling the dielectric barrier discharge gas outlet to export a predetermined amount of the ROS-dominated reactive gas through the dielectric barrier discharge controllable flow gas pump; and mixing the RNS-dominated reactive gas and the ROS-dominated reactive gas in the reactive gas mixing chamber according to a mixing ratio to form the RNS/ROS mixed reactive gas, wherein the mixing ratio is as follows:

the volume ratio of the ROS-dominated reactive gas to the RNS-dominated reactive gas is greater than or equal to $$\frac{0.556b + 0.051c}{0.328a},$$

a being an absorption value of a Fourier infrared absorption spectrum of the ROS-dominated reactive gas at the position with a wave-number of $1055 \text{ cm}^{-1}$, b being an absorption value of a Fourier infrared absorption spectrum of the RNS-dominated reactive gas at the position of a wave-number of $1630 \text{ cm}^{-1}$, and c being an absorption value of a Fourier infrared absorption spectrum of the RNS-dominated reactive gas at the position of a wave-number of $1900 \text{ cm}^{-1}$, and the RNS/ROS mixed reactive gas is directly configured to perform disinfection, or is configured to process an aqueous solution and then perform disinfection by using plasma-activated water.

More preferably, the method further includes the following steps:

importing RNS/ROS mixed reactive gas into an activated water disinfection unit and/or a gas injection disinfection unit and/or a gas filling disinfection unit through an outlet of a reactive gas mixing unit.

More preferably, plasma generated through discharging of the gliding arc plasma source belongs to warm plasma, and a microwave plasma source may be configured to generate warm plasma, wherein the microwave plasma source includes a microwave source, a resonant cavity and the like.

Beneficial Effects

1. In the present disclosure, two plasma sources respectively generate the plasma reactive gas dominated by nitrogen oxide and the plasma reactive gas dominated by ozone in two different discharge modes, and the nitrogen oxide reactive gas and ozone reactive gas are mixed. Compared with single discharge mode, the method may generate two kinds of reactive species which are difficult to generate by a single discharge form, so that the solubility (as shown in FIG. 2) of the reactive species from the mixed reactive gas generated under the same power in the aqueous solution may be greatly enhanced, and the use efficiency of the reactive species may be improved.

2. In the present disclosure, two plasma sources adopt discharge structures suitable for their respective modes. After the whole set of system is started, the ozone mode high-voltage power supply and nitrogen oxide mode high-voltage power supply may enable the two plasma sources to automatically achieve a stable ozone mode discharge state and a nitrogen oxide mode discharge state respectively. The above discharge states are insusceptible to the external environment, and the discharge stability is greatly improved. Therefore, it is unnecessary to regulate or control the discharge environment, and the cost of a control system in the device is saved. Compared with the method, the intermediate state discharge mode of the ozone mode and the nitrogen oxide mode can also obtain the mixed reactive gas similar to the present disclosure, but a power and temperature control system with high precision need to be adopted, so the cost is extremely high, and the tolerance to external environment interference is low.

3. In the present disclosure, the mixed reactive gas with a large number of high-valence and strong oxidizing nitrogen oxides may be generated. Several studies have shown that the above high-valence nitrogen oxides have a long lifetime in water, which can induce oxidative stress of bacteria and play a key role in sterilization. Compared with the single use of the nitrogen oxide reactive gas or ozone reactive gas for disinfection, the present disclosure has a stronger sterilization effect (as shown in FIG. 3).

4. In the present disclosure, the plasma mixed reactive gas may be applied to various disinfection occasions, and the gas or water sterilization and disinfection methods may be flexibly selected. It is only necessary to change the reactive gas disinfection unit structure to realize various implementation methods such as preparation of activated water for disinfection or disinfection and preservation for closed space. For example: the mixed reactive gas is treated by a gas washing device so as to prepare plasma-activated water for spraying, soaking, and smearing disinfection; the mixed reactive gas is connected to a jet head so as to perform disinfection on a moist/water-containing object surface (such as skin); and the mixed reactive gas is introduced into a closed chamber, and the inside of the chamber is humidified so that the closed space can be disinfected, or objects (such as vegetable and fruit) stored in the space can be kept fresh.

5. In the present disclosure, the ambient air is used as a gas source, which may be obtained in a large quantity from the surrounding natural environment; the device is simple to operate and may automatically reach the working condition once started without manual control; and the device is simple in structure and low in production and maintenance cost.

6. The plasma mixed reactive gas generated by the above method is used for disinfection and sterilization, which is non-toxic and reliable to the human body and the environment, and can play a good role in environmental disinfection, food preservation and anti-infection treatment of diseased parts.

7. The present disclosure adopts the internal recycle system, the mixed reactive gas in which the reactive nitrogen species and the reactive oxygen species coexist may completely increase the concentration of the reactive nitrogen species and the reactive oxygen species in the gas circuit through the internal recycle system, and can be mixed and in contact with the aqueous solution completely to enhance the dissolution of the reactive species in water so that the sterilization effect of the prepared reactive aqueous solution is obviously improved.

BRIEF DESCRIPTION OF THE DRAWINGS

It becomes clear for a person of ordinary skill in the art to learn various other advantages and benefits by reading the detailed description of the following preferred specific implementations. The accompanying drawings are merely used to show the preferred implementations and are not considered as limitations to the present disclosure. Apparently, the accompanying drawings in the following description show merely some embodiments of the present disclosure, and a person of ordinary skill in the art may still derive other drawings from these accompanying drawings without creative efforts. In addition, in all of the accompanying drawings, the same parts are represented by the same reference numerals.

In the accompanying drawings:

FIGS. 2A-2C are the Fourier Infrared (FTIR) absorption spectra of the gas before and after the water respectively treated, wherein FIG. 2A shows the FITR absorption spectra by the combination of the nitrogen oxide mode and the ozone mode (mixed mode), FIG. 2B shows the FITR absorption spectra by the single nitrogen oxide mode, and FIG. 2C shows the FITR absorption spectra by the ozone mode under the same power conditions in another embodiment of the present disclosure;

(the adopted volume ratio of RNS-dominated reactive gas to the ROS-dominated reactive gas is equal to 1:3), and is a comparison diagram of the sterilization effect of the mixed ratio not meeting the above condition on methicillin-resistant *Staphylococcus aureus* (MRSA);

The present disclosure is further described below with reference to the accompanying drawings and embodiments.

DETAILED DESCRIPTION

The specific embodiments of the present disclosure will be described in detail below with reference to FIG. 1 to FIG. 11. Although the accompanying drawings show the specific embodiments of the present disclosure, it should be understood that the present disclosure may be implemented in various forms and shall not be limited by the embodiments described herein. On the contrary, these embodiments are provided to provide a more thorough understanding of the present disclosure, and the scope of the present disclosure can be fully conveyed to those skilled in the art.

It should be noted that some words are used in the specification and the claims to refer to specific components. It should be understood by those skilled in the art that technicians may use different nouns to refer to the same component. The specification and the claims do not use noun difference as a way of distinguishing components, but use function difference as a criterion for distinguishing the components. The word "comprise" or "include" as used throughout the specification and claims is an open term and should be interpreted as "including but not limited to". The subsequent description of the specification is preferred implementation of the present disclosure. However, the description takes the general principles of the specification as the objective, and is not intended to limit the scope of the present disclosure. The protection scope of the present disclosure is defined by the appended claims.

In order to facilitate the understanding of the embodiments of the present disclosure, the specific embodiments will be taken as examples for further explanation and description with reference to the accompanying drawings, and the drawings do not constitute a limitation to the embodiments of the present disclosure.

Figure 1:
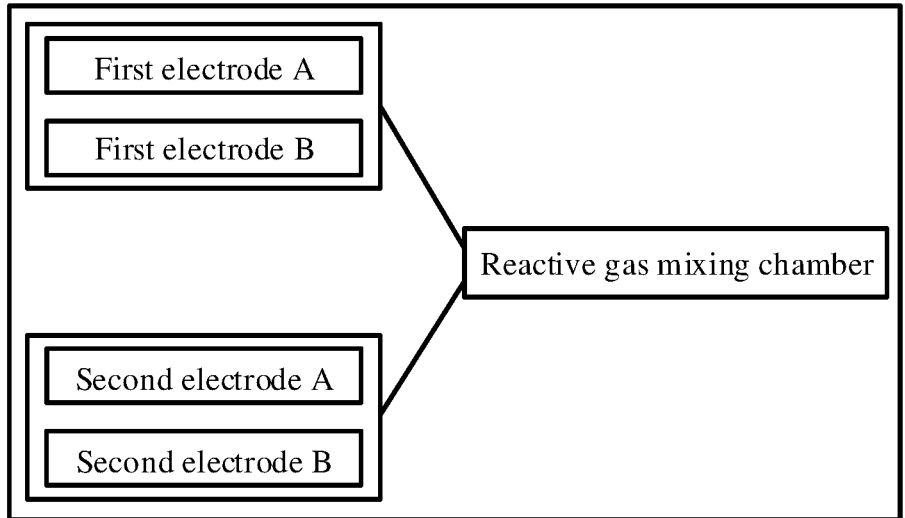
FIG. 1 is a structural schematic diagram of a disinfection device in an embodiment of the present disclosure.

As shown in FIG. 1, a gliding arc and dielectric barrier discharge combined discharge plasma disinfection device includes:

the first A electrode and the first B electrode used for: generating a first plasma gas under a first voltage, wherein the first plasma gas is mainly produced by nitrogen oxide;

the second A electrode and the second B electrode used to generate a second plasma gas under a second voltage, wherein the second plasma gas is dominated by ozone; the reactive gas mixing chamber is used to mix the first plasma gas and the second plasma gas to form a mixed reactive gas, wherein the mixed reactive gas can be directly used for disinfection and sterilization, or the aqueous solution can be processed first, and then used plasma activated water disinfection and sterilization.

For the above embodiment, the intermediate state mode in the air discharge mode is discarded.

The prior art usually adopts an intermediate state mode discharge, because the intermediate state mode can directly generate a mixed gas of ozone and nitrogen oxides to obtain reactive gas with higher activity, so the disinfection effect can be improved. However, the inventor has realized that this has the following problem: Although the plasma disinfection device in the intermediate mode can directly obtain a higher reactive gas, it is precisely because of its high reactivity that this type of disinfection device is extremely sensitive. In the prior art, this type of disinfection device directly generates gases including ozone and nitrogen oxides, and a series of chemical reactions occur between the two themselves, and the rate constant and equilibrium constant of the reaction are extremely sensitive to parameters such as temperature and power. Fluctuations in the final product will result in greater changes in the composition of the final product. Therefore, in the prior art, this type of disinfection device needs to use a high-precision power and temperature control system, which is extremely costly and still has a low tolerance to external environmental interference.

The above embodiment creatively proposes a new disinfection device, which essentially includes two plasma generators, which are used to generate the corresponding plasma reactive gas dominated by nitrogen oxide (mainly NO and $NO_2$) and the plasma reactive gas dominated by ozone in their respective discharge modes. Since these two reactive gases are produced independently, and before mixing, the two reactive gases have lower solubility and poor biological reactivity, which means that the present disclosure creatively proposes a technical solution of separately generating two reactive gases and then mixing them, thereby avoiding the problem of precise control and extremely sensitiveness in the prior art that the disinfection device must be controlled.

In other words, the inventors of the present disclosure make full use of the knowledge and experience of the air discharge modes include ozone mode, intermediate state mode and nitrogen oxide mode. With the change of external conditions such as temperature increase and power increase, the plasma gradually changes from ozone mode to intermediate state mode and then to nitrogen oxide mode. The inventors creatively abandoned the commonly used intermediate state mode and replaced it with the ozone mode and the nitrogen oxide mode at both ends of the intermediate state mode, thus overcoming the technical prejudices in this field. The inventive concept that the two gases are then mixed again, so that the disinfection device of the present disclosure still finally obtains a mixed reactive gas mixed with ozone and nitrogen oxide. For those skilled in the art, the gas mixed with ozone and nitrogen oxides naturally has the effect of disinfection and sterilization. Therefore, the above-mentioned embodiment of the present disclosure also achieves the effect of disinfection and sterilization.

In the embodiment of the present disclosure, in the ozone mode and the nitrogen oxide mode, the discharge products are respectively dominated by ozone and nitrogen oxides. The above two types of discharge products do not undergo chemical reactions themselves, so when far away from the critical conditions of mode conversion, a relatively stable discharge state can be achieved, and is not susceptible to external influences such as environmental temperature changes or power fluctuations, so there is no need to perform precise control of the discharge environment. As mentioned above, it can be understood that the present disclosure first generates stable reactive gas in ozone mode and reactive gas in nitrogen oxide mode and then mixes them to obtain mixed reactive gas, which has lower control cost and higher Robustness.

Furthermore, in another embodiment, the first plasma gas and the second plasma gas are mixed as follows:

the volume of the ozone reactive gas: the volume of the nitrogen oxide reactive gas $$\geq \frac{0.556b + 0.051c}{0.328a},$$

wherein a is an absorption value of a Fourier infrared absorption spectrum of the second plasma gas at the position with a wave-number of 1055 $cm^{-1}$, b being an absorption value of a Fourier infrared absorption spectrum of the first plasma gas at the position of a wave-number of 1630 $cm^{-1}$, and c being an absorption value of a Fourier infrared absorption spectrum of the first plasma gas at the position of a wave-number of 1900 $cm^{-1}$.

For this embodiment, this is an empirical formula obtained from a large number of experiments, and the purpose is to make the mixed reactive gas include high-valence nitrogen oxides ($N_2O_5$, etc.). Because high-valence nitrogen oxides are highly oxidizing and have a long life in water (>10 minutes), and many studies have shown that these high-valence nitrogen oxides can induce bacterial oxidative stress and play a key role in sterilization.

In the mixed mode of the above embodiment, more high-valence nitrogen oxides can be generated, and thus a better disinfection effect can be obtained. Compared with this embodiment, the prior art adopts the intermediate state discharge mode of the disinfection device. Since the intermediate state mode cannot quantitatively control the proportion of each reactive species, even if the optimal temperature and power are found, it is only effective for a specific plasma generator, which is not universal and universal, and it is difficult to obtain the optimal yield of high-valence nitrogen oxides.

Figure 2A:
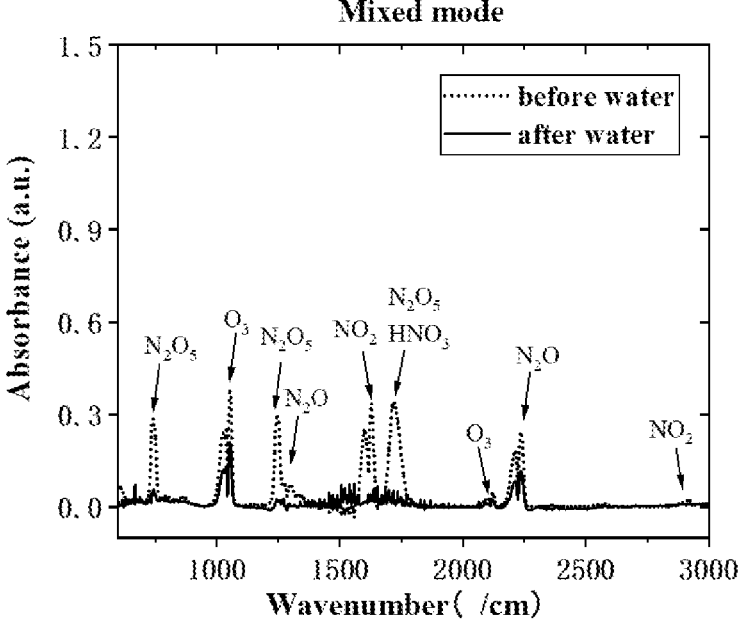
Figure 2B:
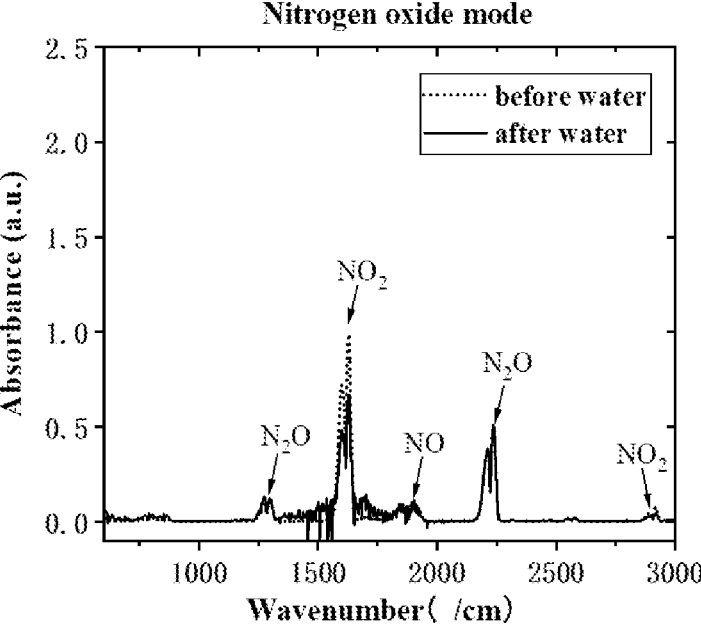
Figure 2C:
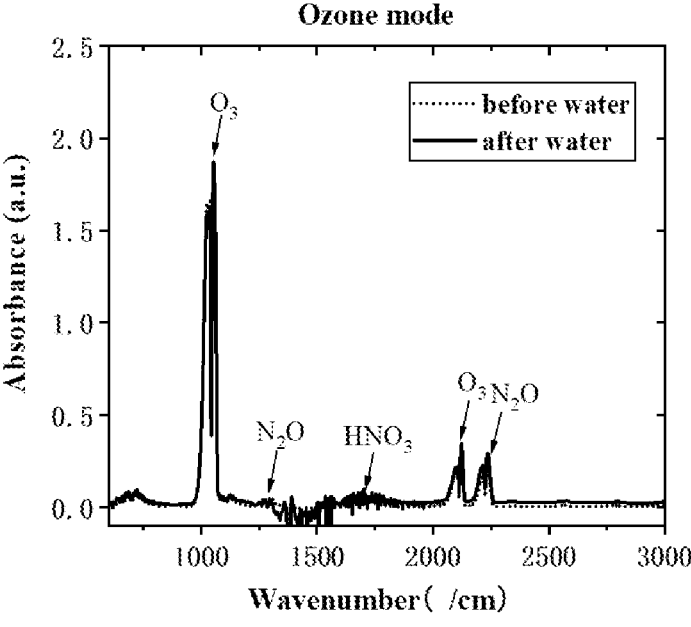

This means that due to the effect of high-valence nitrogen oxides, the mixed reactive gas obtained in this embodiment has a better absorption effect by water than the single-mode reactive gas, which improves the use efficiency and energy efficiency of the reactive species, as shown in FIG. 2. (a) to FIG. 2(c):

FIGS. 2(a), 2(b), and 2(c) are respectively Fourier infrared absorption spectrum comparison diagrams before or after aqueous solution treatment with ozone mode, nitrogen oxide mode, and mixed mode. According to the Lambert-Beer law, in the figure, the absorbance represented by y-coordinate is directly proportional to the concentration of reactive species, the wave-number of the x-coordinate combining with the shape of an absorption peak may determine which type of reactive species each absorption peak represents, and the corresponding relation between the absorption peak and the reactive species has been marked with an arrow in the figure. In the figure, the ratio of the reactive species absorbed by water may be obtained by subtracting the height of the absorption peak after passing through water from the height of the absorption peak before passing through water. It can be seen from the figure that the absorption ratio of $O_3$ by water in the ozone mode reactive gas is less than 5%, and $N_2O$ is absorbed by about 20%; in the nitrogen oxide mode reactive gas, $NO_2$ is absorbed by about 30%, and the remaining reactive species are basically not absorbed; and in the mixed reactive gas in the mixed mode, both $O_3$ and $N_2O$ are absorbed by more than 50%, and $NO_2$, $N_2O_5$, and $HNO_3$ are basically all absorbed.

Figure 3:
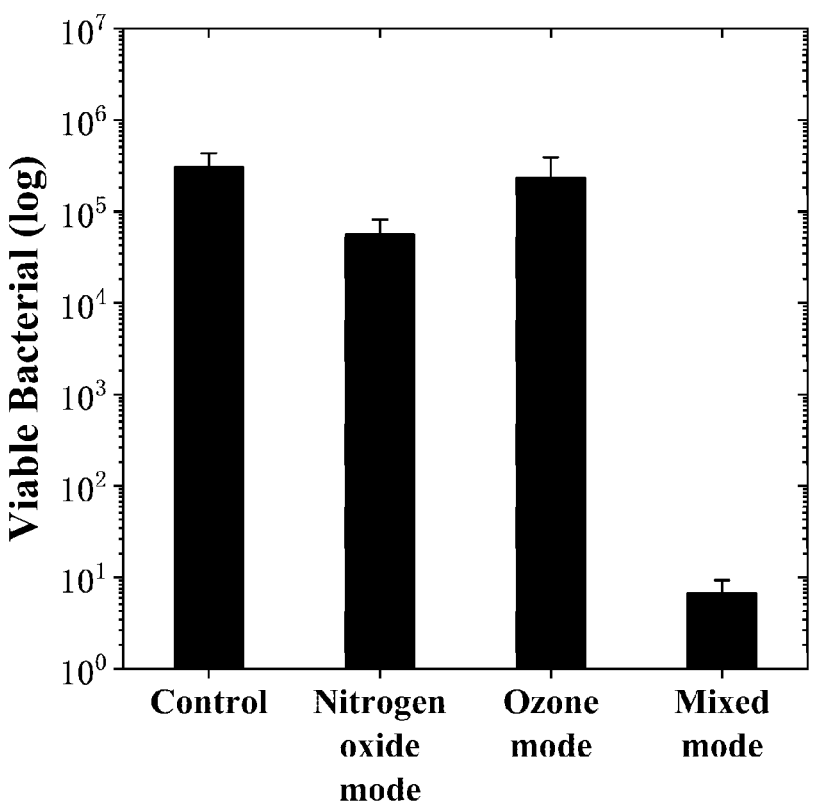
FIG. 3 is a comparison diagram of the combination of the nitrogen oxide mode and the ozone mode, the single nitrogen oxide mode, and the single ozone mode on the sterilization effect of methicillin-resistant *Staphylococcus aureus* (MRSA) according to an embodiment of the present disclosure.

In addition, compared with the activated water prepared by using a single mode of reactive gas, the activated water prepared by further using the reactive gas in this embodiment has a stronger sterilization and disinfection effect, as shown in FIG. 3.

In summary, the plasma mixed reactive gas produced by the present disclosure can be used in a variety of disinfection occasions, and the mode of gas or water disinfection can be flexibly selected. Only the structure of the reactive gas disinfection and sterilization unit needs to be changed to realize the preparation of activated water disinfection and closed space disinfection and preservation. For example, the mixed reactive gas is treated with a gas scrubbing device to prepare plasma-activated water that can be used for spraying, soaking, and smearing disinfection. Compared with the activated water prepared by the traditional method, the disclosure can produce more high-valence nitrogen oxides and has a better disinfection effect. For another example, if the mixed reactive gas is connected to a spray head and sprayed out, the surface of wet/water-containing objects (such as skin) can be sprayed and disinfected; or the mixed reactive gas can be passed into a closed chamber and the inside of the chamber can be humidified at the same time, then it can disinfect the confined space or keep the storage in the space (such as vegetables and fruits) fresh. Traditional plasma dry sterilization requires that the plasma jet plume directly contact the object to be sterilized, or the discharge electrode is close to the object, however, the present disclosure uses a mixed reactive gas for sterilization, which eliminates the risk of electric shock in the traditional method and broadens the application range of plasma disinfection, such as disinfection and preservation of the interior of the chamber.

In another embodiment, the first plasma gas is dominated by nitrogen oxides, preferably nitrogen oxides account for more than 90% of the total plasma discharge products.

In another embodiment, the second plasma gas is dominated by ozone, and preferably ozone accounts for more than 80% of the total products of the plasma discharge.

It can be understood that taking nitrogen oxides as the dominant product means that nitrogen oxides dominate. For example, nitrogen oxides account for more than 50% among all the discharge products. Similarly, taking ozone as the dominant product means that ozone is dominant. For example, ozone accounts for more than 50% among all the discharge products. The 80% and 90% mentioned here are more preferred embodiments.

Obviously, the dominant product actually restricts all possible specific embodiments of this embodiment. The possible specific embodiments involve many factors. Taking the air discharge mode as an example, the discharge plasma is affected by many factors. Typical factors include temperature and power. In addition, there are electrode shape and size, and whether there is insulation. The type of dielectric layer and insulating medium are related to the thickness, air gap width, gas flow rate, high-voltage power supply type (such as DC, pulse, sine, etc.), high-voltage power supply frequency and many other influencing factors; under the same temperature and power conditions, different high-voltage power supplies applied to different plasma sources will produce completely different discharge modes, so the range of a single variable cannot be the decisive control factor of the discharge mode in the present disclosure. It is actually very suitable to use nitrogen oxides and ozone as the main products respectively to constrain the constraints of various possible specific embodiments. The following text will also exemplarily enumerate the corresponding embodiments, but just as the inventive concept disclosed above, the inventor must point out that the inventive concept of the present disclosure is not limited by these specific embodiments.

Figure 4:
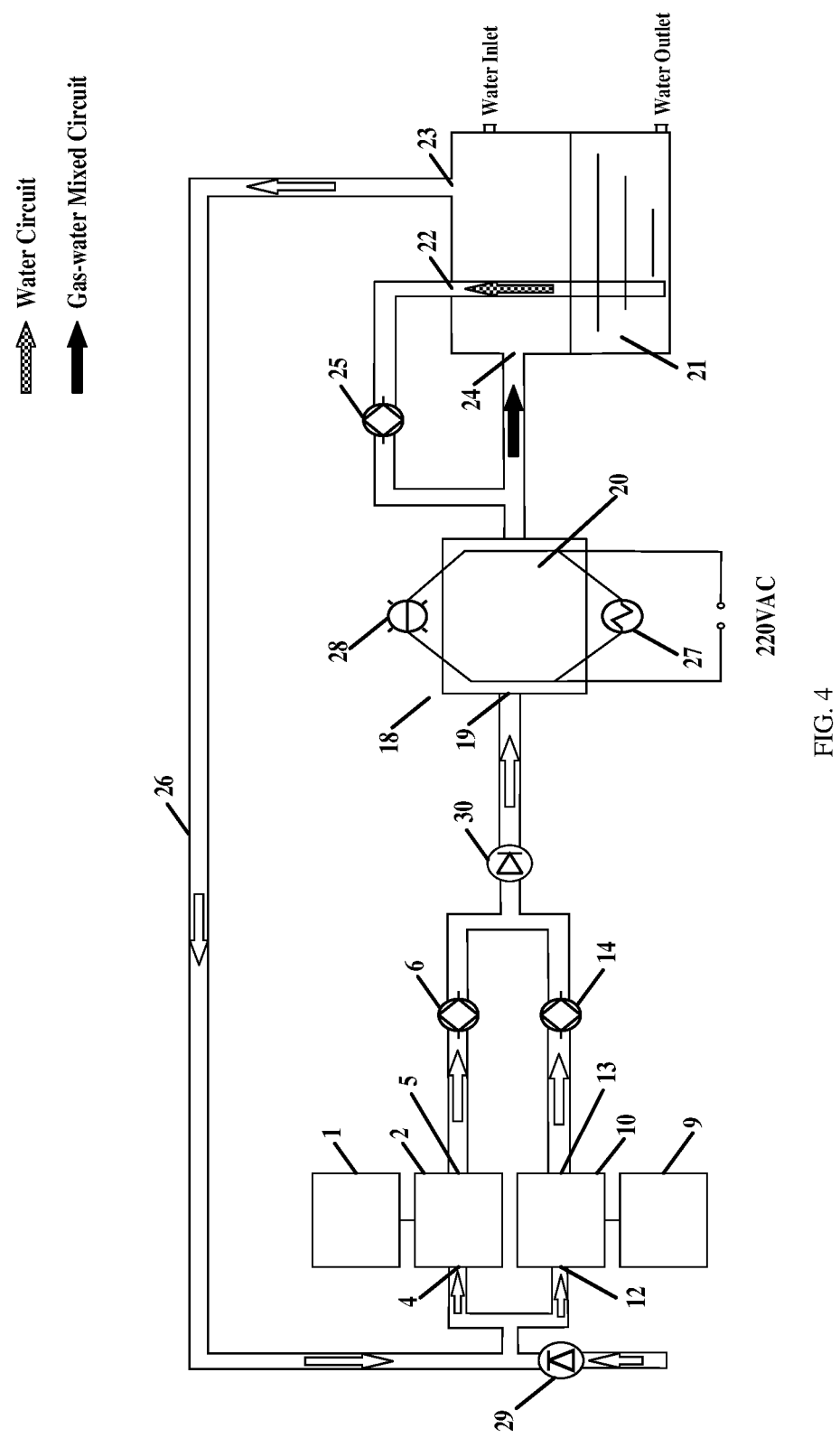
FIG. 4 is a structural schematic diagram of a disinfection device in another embodiment of the present disclosure.
Figure 5:
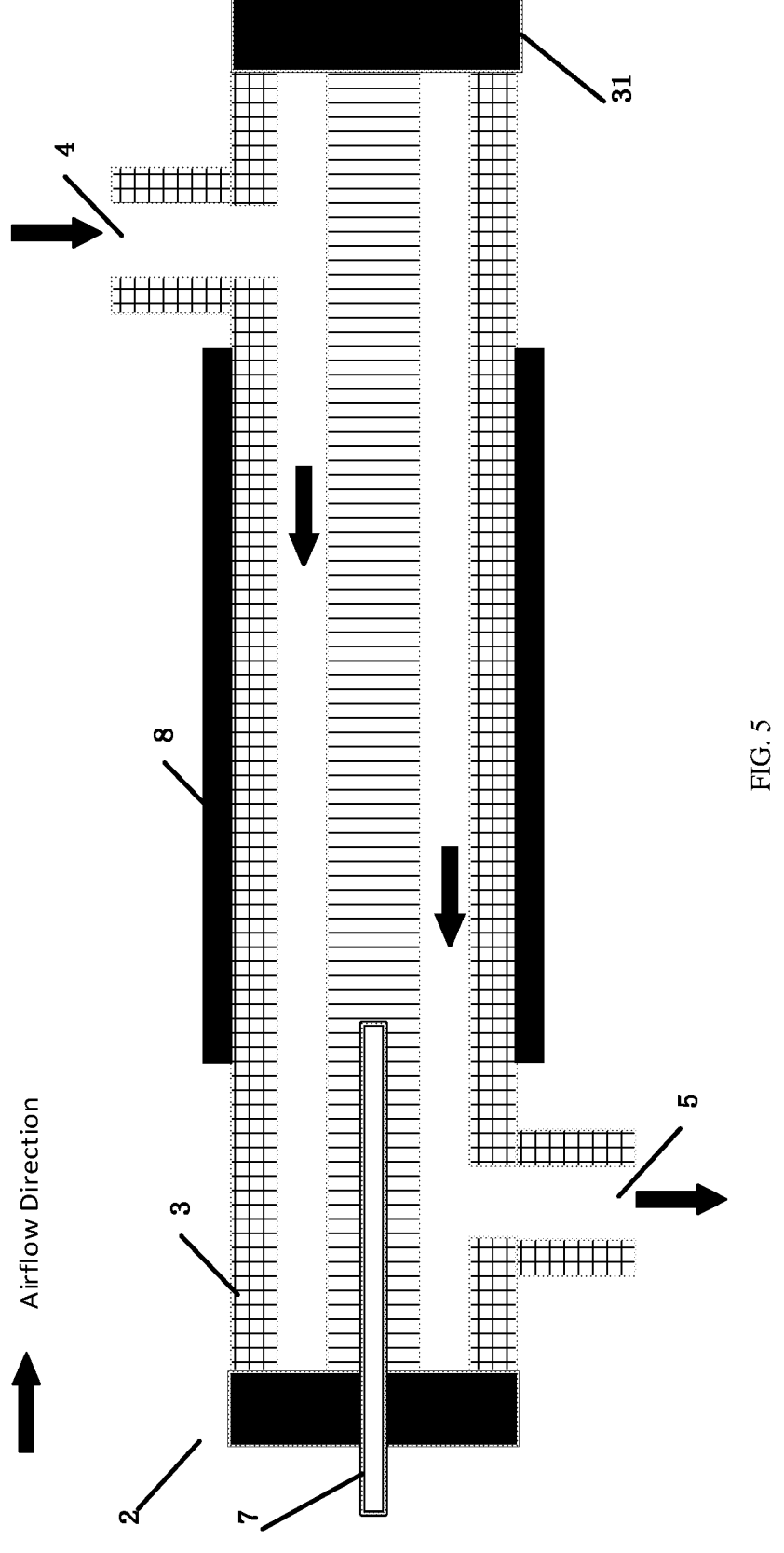
FIG. 5 is a structural schematic diagram of the first plasma source of the disinfection device in another embodiment of the present disclosure.
Figure 6:
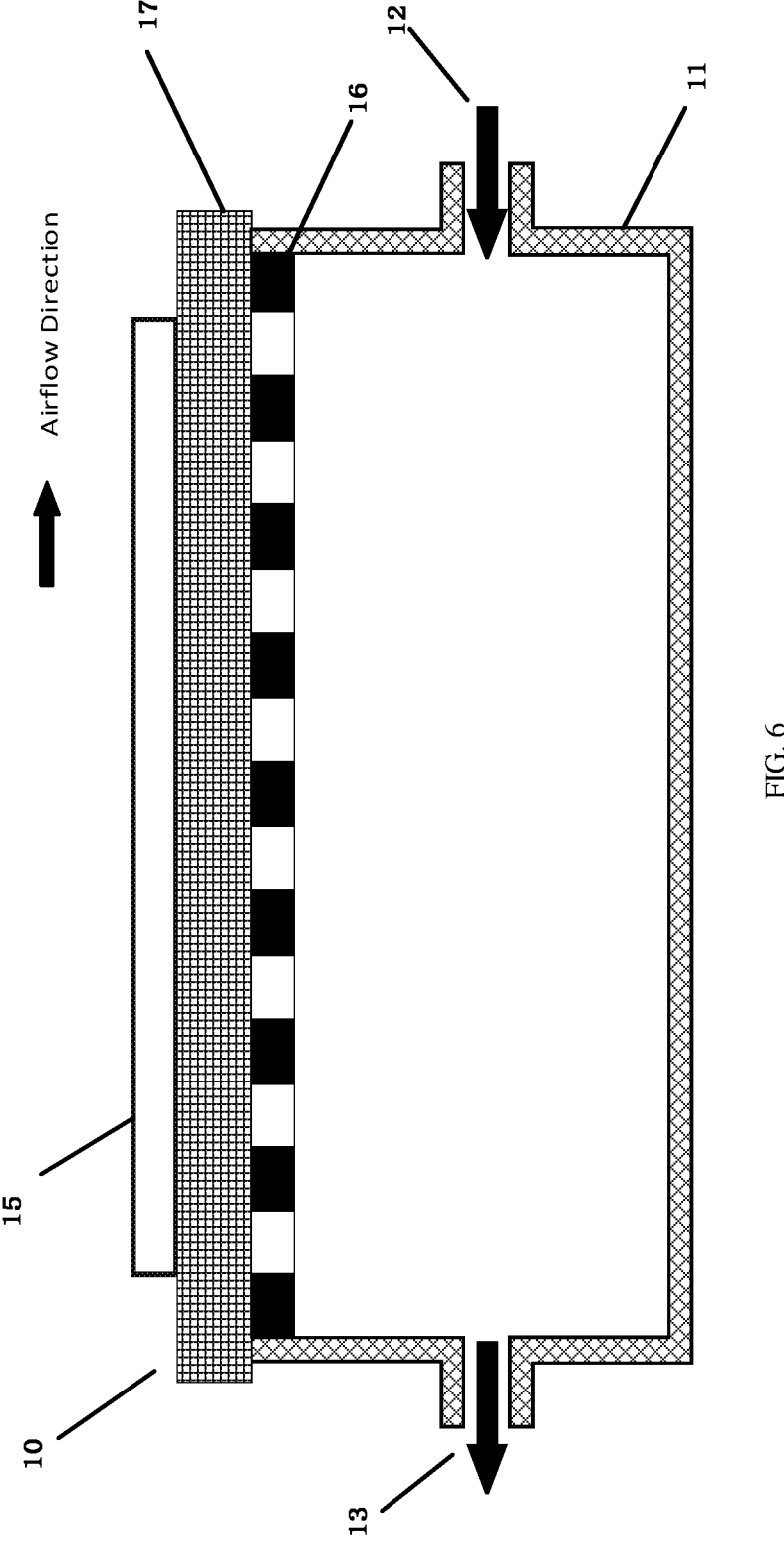
FIG. 6 is a structural schematic diagram of the second plasma source of the disinfection device in another embodiment of the present disclosure.

Referring to FIG. 4, FIG. 5, and FIG. 6, in another embodiment, a discharge plasma disinfection device combining nitrogen oxide mode and ozone mode includes:

the first high-voltage power supply 1, configured to provide a first voltage, the first plasma source 2, connected to the first high-voltage power source 1, and the first plasma source 2 includes, the first plasma chamber 3, provided with a first air inlet 4 and a first air outlet 5, and the first air outlet 5 is connected to a first controllable flow air pump 6, the first A electrode 7, connected to the first high-voltage power supply 1, the first B electrode 8, connected to the first high-voltage power supply 1, the first B electrode 8 and the first A electrode 7 generate a first plasma gas at a first voltage, and the first plasma gas is nitrogen Oxide is the leading product;

the second high-voltage power supply 9, configured to provide a second voltage;

the second plasma source 10, connected to the second high voltage power source 9, and the second plasma source 10 includes:

the plasma chamber 11, provided with a second air inlet 12 and a second air outlet 13, and the second air outlet 13, connected to a second controllable flow air pump 14, the second A electrode 15, connected to the second high voltage power source 9, the second B electrode 16, connected to the second high-voltage power supply 9, an insulating dielectric plate 17, arranged between the second A electrode 15 and the second B electrode 16, the second A electrode 15 and the second B electrode 16 generate a second plasma gas under a second voltage, and the second plasma gas is mainly produced by ozone;

reactive gas mixing unit 18, which includes, the inlet 19, connected to the first controllable flow air pump 6 and the second controllable flow air pump 14, the reactive gas mixing chamber 20, connected to the inlet 19 to mix the first plasma gas and the second plasma gas to form a mixed reactive gas.

Among them, the dominant product means that its proportion in all the discharge products is at least more than 50%. The device controls the power density, gas temperature, and other discharge conditions of the two plasma generators, so that the nitrogen oxide mode and ozone mode plasma generation units respectively generate the plasma reactive gas dominated by nitrogen oxide and the plasma reactive gas dominated by ozone. Under the action of the controllable flow air pump, the two plasma reactive gases are mixed in the reactive gas mixing unit 18 at a specific ratio, so that the mixed reactive gas contains a large number of nitrogen oxides and ozone at the same time, and a large amount of high-valence nitrogen oxides with strong sterilization effect such as $NO_3$, $N_2O_5$, etc. are produced, and enter the reactive gas disinfection and sterilization unit to achieve various methods and uses of sterilization and disinfection. The mixed reactive gas can be used for direct disinfection and sterilization, or the aqueous solution is processed first, and then the plasma-activated water is used for disinfection and sterilization. The device and method use ambient air as a raw material, and have the advantages of high reactive species yield, strong permeability, good device sterilization effect and stable performance.

In a preferred embodiment of the discharge plasma disinfection device combining the nitrogen oxide mode and the ozone mode, the disinfection device further includes an activated water disinfection and sterilization unit, which is connected to the outlet of the reactive gas mixing unit 18 to introduce mixed reactive gas. The activated water disinfection and sterilization unit includes, the activated water preparation chamber 21, which contains the solution and is provided with a circulating water outlet 22, a gas return port 23 and a gas-liquid mixture inlet 24, the peristaltic water pump 25, which has one end connected to the outlet of the reactive gas mixing unit 18, and the other end connected to the circulating water outlet 22 of the activated water preparation chamber 21 to pump the solution to form a gas-liquid mixture, and return to the activated water preparation chamber 21 through the gas-liquid mixture inlet 24, the air return passage 26, one end of which is connected to the air return port 23 and the other end is connected to the first air inlet 4 and the second air inlet 12 to circulate activated water to prepare the gas in the cavity 21.

In a preferred embodiment of the discharge plasma disinfection device combining the nitrogen oxide mode and the ozone mode, the first high-voltage power supply 1 includes a sinusoidal power supply, a radio frequency power supply or a DC power supply. The voltage of the first high-voltage power supply 1 is above 10 kV, and the output power is above 200 W, the voltage of the second high-voltage power supply 9 is above 5 kV, and the output power is above 8 W.

In a preferred embodiment of the discharge plasma disinfection device combining the nitrogen oxide mode and the ozone mode, the disinfection device further includes a gas spray disinfection unit and/or a gas filling disinfection unit based on the mixed reactive gas, which are all connected to the outlet of the reactive gas mixing unit 18.

In a preferred embodiment of the discharge plasma disinfection device combining the nitrogen oxide mode and the ozone mode, the mixing ratio of the first plasma gas and the second plasma gas into the reactive gas mixing unit 18 is:

the volume of the ozone reactive gas: the volume of the nitrogen oxide reactive gas $$\geq \frac{0.556b + 0.051c}{0.328a},$$

wherein a is an absorption value of a Fourier infrared absorption spectrum of the second plasma gas at the position with a wave-number of 1055 $cm^{-1}$, b being an absorption value of a Fourier infrared absorption spectrum of the first plasma gas at the position of a wave-number of 1630 $cm^{-1}$, and c being an absorption value of a Fourier infrared absorption spectrum of the first plasma gas at the position of a wave-number of 1900 $cm^{-1}$.

In a preferred embodiment of the discharge plasma disinfection device combining the nitrogen oxide mode and the ozone mode, the reactive gas mixing chamber further includes, the heater 27, which heats the mixed reactive gas in the reactive gas mixing chamber, and controls the temperature of the reactive gas mixing chamber to 30-50 DEG C. to maintain a high chemical reaction rate and prevent ozone from decomposing at high temperatures, the ultraviolet lamp 28, which irradiates the mixed reactive gas.

In a preferred embodiment of the discharge plasma disinfection device combining the nitrogen oxide mode and the ozone mode, the first air inlet and the second air inlet are connected to a supplementary valve 29, and the supplementary valve 29 has no opening air pressure. The outlet of the one-way valve is connected with the first air inlet 4 and the second air inlet 12.

For the above embodiments, the reaction between ozone and nitrogen oxides is non-unidirectional, slower and simple. Therefore, in order to quickly generate more high-valence nitrogen oxides, this embodiment uses a heater to increase the temperature of the reaction chamber to accelerate the chemical reaction rate, while controlling the maximum temperature to prevent ozone decomposition; in addition, UV lamps are used to photodecompose oxygen in the gas into oxygen atoms, which further promotes the formation of high-valence nitrogen oxides.

In a preferred embodiment of the discharge plasma disinfection device combining the nitrogen oxide mode and the ozone mode, the first controllable flow air pump 6 and the second controllable flow air pump 14 are connected to the inlet 19 via a check valve 30.

In a preferred embodiment of the discharge plasma disinfection device combining the nitrogen oxide mode and the ozone mode, the first plasma source 2 includes a sealed end 31 that seals the first plasma chamber 3.

In one embodiment, the device includes a nitrogen oxide mode plasma generating unit, an ozone mode plasma generating unit, a reactive gas mixing unit 18, and a reactive gas disinfection and sterilization unit. The nitrogen oxide mode plasma source is used for discharging under the driving of the nitrogen oxide mode high-voltage power supply, and generates a plasma reactive gas dominated by nitrogen oxide. Nitrogen oxide mode plasma source can choose dielectric barrier discharge, radio frequency discharge or gliding arc discharge and other discharge methods that can generate a large amount of nitrogen oxide. The oxynitride mode high-voltage power supply is used for the discharge power of the nitrogen oxide mode plasma source. It can generate a high voltage power supply of 10 kV and above, can provide an output power of more than 200 W, and can resist the voltage fluctuation caused by the temperature change of the nitrogen oxide mode plasma source. Nitrogen oxide mode high voltage power supply can choose sinusoidal power supply, radio frequency power supply or DC power supply.

The ozone mode plasma source, used for discharging under the drive of the ozone mode high-voltage power supply to generate the plasma reactive gas dominated by ozone. The ozone mode plasma source can choose a discharge method that can generate a large amount of ozone, such as dielectric barrier discharge, jet discharge, or corona discharge. The ozone mode high-voltage power supply is used for the discharge power of the ozone mode plasma source. It can generate a high-voltage power supply of 5 kV and above, can provide an output power of more than 8 W, and can resist the voltage fluctuation caused by the temperature change of the ozone mode plasma source.

The reactive gas mixing chamber 20 is used to contain the reactive gases from the two plasma generators, and serves as a reaction chamber for the two reactive gases.

The heater 27 is used to heat the mixed reactive gas in the reactive gas mixing chamber 19, controlling the temperature at 30-50 degrees Celsius, and speeding up the thermal movement of the mixed reactive gas without damaging the reactive gas in the chamber and causing it to decompose and fail. Promote the reaction of two reactive gases, thereby increasing the yield of high-valence nitrogen oxides.

The ultraviolet lamp 28, used to enhance the reaction degree of the mixed reactive gas. The ultraviolet light decomposes the oxygen molecules in the air to generate free oxygen atoms, namely reactive oxygen, which further strengthens the oxidation of the nitrogen oxide reactive gas, thereby increasing the yield of high-valence nitrogen oxides.

The reactive gas disinfection and sterilization unit can be used for direct gas disinfection or treatment of aqueous solutions to obtain plasma-activated water for indirect disinfection and disinfection.

When direct sterilization and disinfection by gas, the implementation of the reactive gas disinfection and sterilization unit includes but is not limited to: disinfection of the wet surface by reactive gas injection, disinfection of objects in the space by filling the reactive gas into a closed space or keep fresh.

When the treated aqueous solution is indirectly sterilized and disinfected by plasma-activated water, tap water, ultrapure water, deionized water, medical physiological saline, alcohol solution or diluted $H_2O_2$ can be activated. The implementation of activated water sterilization and disinfection includes, but is not limited to: sterilization or disinfection by washing, spraying, and soaking.

The disinfection device controls the voltage and power of the two plasma generators, so that the high and ozone mode plasma generating units respectively generate the plasma reactive gas dominated by nitrogen oxide and the plasma reactive gas dominated by ozone. Under the action of the controllable flow air pump, the two plasma reactive gases are mixed in the reactive gas mixing unit 18 in a specific proportion to generate a large amount of high-valence nitrogen oxides with strong oxidizing and bactericidal property, and enter the reactive gas disinfection and sterilization unit to realize sterilization and disinfection in various ways and purposes.

A method for a discharge plasma disinfection device combining nitrogen oxide mode and ozone mode includes the following steps:

the first high-voltage power supply 1 provides a first voltage, the first plasma source 2 generates a first plasma gas, and the first plasma gas takes nitrogen oxide as the main product, and the second high-voltage power supply 9 provides a second voltage. Plasma source 10 generates a second plasma gas, and the second plasma gas uses ozone as the dominant product;

the first gas outlet 5 derives a first predetermined amount of first plasma gas via a first controllable flow gas pump 6, and the second gas outlet 13 derives a second predetermined amount of second plasma gas via a second controllable flow gas pump 14. The reactive gas mixing chamber 20 forms a mixed reactive gas from the first plasma gas and the second plasma gas according to the mixing ratio, wherein the volume of the ozone reactive gas: the volume of the nitrogen oxide reactive gas $$\geq \frac{0.556b + 0.051c}{0.328a},$$

wherein a is an absorption value of a Fourier infrared absorption spectrum of the second plasma gas at the position with a wave-number of 1055 cm$^{-1}$, b being an absorption value of a Fourier infrared absorption spectrum of the first plasma gas at the position of a wave-number of 1630 cm$^{-1}$, and c being an absorption value of a Fourier infrared absorption spectrum of the first plasma gas at the position of a wave-number of 1900 cm$^{-1}$, the mixed reactive gas is introduced into the activated water disinfection and sterilization unit and/or the gas jet disinfection unit and/or the gas filling and disinfection unit through the outlet of the reactive gas mixing unit 18.

In the preferred embodiment of the method, the two plasma discharge modes are performed simultaneously. The nitrogen oxide mode plasma generating unit generates reactive gas with nitrogen oxide as the main product, and the ozone mode plasma generating unit generates the reactive gas with ozone as the main product;

the two reactive gases enter the reactive gas mixing unit 18 in the following proportions:

the volume of the ozone reactive gas: the volume of the nitrogen oxide reactive gas $$\geq \frac{0.556b + 0.051c}{0.328a},$$

where, a is an absorption value of a Fourier infrared absorption spectrum of the second plasma gas at the position with a wave-number of 1055 cm$^{-1}$, b is an absorption value of a Fourier infrared absorption spectrum of the first plasma gas at the position of a wave-number of 1630 cm$^{-1}$, c is an absorption value of a Fourier infrared absorption spectrum of the first plasma gas at the position of a wave-number of 1900 cm$^{-1}$;

after entering the activated gas mixer, the two reactive gases fully react to produce the strong oxidizing and bactericidal effect of high-valence nitrogen oxides;

the mixed and reacted reactive gas enters the reactive gas disinfection and sterilization unit through gas spraying, gas filling, etc., or after preparing plasma-activated water, it is disinfected and sterilized by washing, soaking, spraying, etc.

In another embodiment:

a high-voltage sinusoidal power supply of 15 kV, 40 kHz, 250 W is applied to the nitrogen oxide mode plasma source, so that the nitrogen oxide mode plasma source generates a plasma reactive gas dominated by nitrogen oxide. A high-voltage power supply of 7 kV, 20 kHz, and 9 W is applied to the ozone mode plasma source, so that the ozone mode plasma source generates a plasma reactive gas dominated by ozone.

Further, in another embodiment, the controllable flow gas pumps 1 and 2 respectively control the gas flow rate through the plasma source to 1 SLM and 3 SLM. Under the action of the controllable flow air pump, the two reactive gases enter the reactive gas mixing unit 18 through the one-way valve 25 to mix and react, and under the action of the gas heater 27 and the ultraviolet lamp 28, the reaction becomes more violent and sufficient, and high concentration of high-valence nitrogen oxide is generated. The aqueous solution in the activated water preparation chamber 21 fully reacts with the mixed reactive gas under the pumping of the peristaltic water pump 25 to improve the solubility of the reactive species in the aqueous solution, and the aqueous solution is set to 50 mL. After the reaction, the exhaust gas is dried and then re-entered into the intake end of the plasma source through the gas circuit for recycling. The discharge working time is set to 10 min. The prepared plasma-activated water can be used to achieve disinfection on various occasions.

The following are examples of two typical ozone mode plasma generators:

(1) In One Embodiment, for the Ozone Mode Plasma Generator:

A quartz tube with an inner diameter of 3 mm and an outer diameter of 5 mm and a length of 20 cm is coaxially placed inside a 0.8 mm diameter tungsten rod as a high-voltage electrode. The outer wall of the quartz tube is pasted with a 15 cm-long copper foil as a ground electrode; both ends of the quartz tube are connected to air pipes. When working, a 3 L/min airflow is passed through the quartz tube; the high-voltage power supply adopts a 4 kHz square wave pulse power supply with a duty ratio of 50% and a power of 8 W; plasma is generated inside the quartz tube during discharge.

(2) In Another Embodiment, for the Ozone Mode Plasma Generator:

1 mm thick flat copper high voltage electrode, 1 mm thick alumina ceramic dielectric plate, 0.5 mm thick hexagonal mesh stainless steel ground electrode closely fits, the mesh ground electrode discharge area is 64 cm²; there is a 2 cm high sealed chamber below the discharge area of the mesh electrode, and the center of the left and right sides of the chamber is equipped with pneumatic connectors, and the air flow of 2 L/min flows through the chamber; the high-voltage power supply adopts a 10 kHz sinusoidal power supply with a power of 20 W; the plasma is generated at the contact surface between the mesh of the mesh electrode and the dielectric plate during discharge.

The following are examples of two typical nitrogen oxide mode plasma generators:

(1) In One Embodiment, for the Nitrogen Oxide Mode Plasma Generator:

Two trapezoidal stainless steel sheets with a thickness of 2 mm, the upper bottom 20 mm and lower bottom 10 mm 40 mm high, are fixed on the same plane, the upper and lower bottom surfaces are coplanar, and the slope is relatively close to the two trapezoids (upper bottom edge) with a 4 mm gap; above the gap there is a jet head with an inner diameter of 1 mm, and the airflow rate is 1 L/min, which sprays vertically downwards. The above components are all fixed in a quartz chamber; the high-voltage power supply adopts a 50 Hz sinusoidal high-voltage power supply with a power of 60 W; during discharge, the two trapezoidal electrodes generate an arc at the nearest point, which is blown to the bottom by the airflow and breaks, and a new arc is continuously circulated in the nearest place.

(2) In Another Embodiment, for the Nitrogen Oxide Mode Plasma Generator:

A quartz tube with an inner diameter of 22 mm and an outer diameter of 26 mm and a length of 25 cm. A stainless steel rod with a diameter of 20 mm is coaxially placed inside as a high-voltage electrode. A layer of stainless steel mesh with a length of 20 cm is attached to the outer wall of the quartz tube as a ground electrode. 1 L/min airflow is passed through the quartz tube; the high-voltage power supply adopts a 50 kHz sinusoidal power supply with a power of 250 W; plasma is generated inside the quartz tube during discharge.

In another embodiment, the aqueous solution is any one of tap water, ultrapure water, deionized water, physiological saline, or diluted hydrogen peroxide solution.

In another embodiment, the high-voltage power supply is either pulse or sinusoidal high-voltage power supply.

Two gliding arc plasma sources and configurations thereof are illustrated as follows:

(1) A Double-Blade Gliding Arc Source:

two trapezoidal stainless steel sheets with a thickness of 2 mm, an upper bottom of 20 mm, a lower bottom of 10 mm, and a height of 40 mm are fixed on the same plane, the upper bottom surface and the lower bottom surface are coplanar, and there is a 4 mm gap at a position of the inclined surface closest to the two trapezoids (the edge of the upper bottom surface); a jet head with an inner diameter of 1 mm is arranged above the gap, the air with a flow of 1 L/min is sprayed vertically downwards, and the above parts are fixed in one quartz chamber; a high-voltage power supply adopts a 50 Hz sine high-voltage power supply with the power of 60 W; and during discharging, the arc is generated at the nearest place of the two trapezoidal electrodes and is blown down by the airflow to be broken, and a new arc generated at the nearest place continuously circulates.

(2) A Spiral Gliding Arc Source:

one conical stainless-steel electrode with a height of 100 mm and a bottom surface diameter of 20 mm is fixed on a quartz cassette, and one end of a cylindrical electrode with a height of 120 mm, an outer diameter of 27 mm and an inner diameter of 25 mm and the conical electrode are concentrically fixed on the quartz cassette and the other end is fixed to another quartz cassette to form a closed chamber. The air with a flow of 1 L/min is sprayed vertically to an electrode axis direction; the high-voltage power supply adopts a 50 Hz sine high-voltage power supply with the power of 60 W; and during discharging, an arc is generated at the nearest place of the two electrodes, that is, the bottom of the conical electrode, and is spirally blown down by the airflow around the electrode axis to be broken, and a new arc generated at the nearest place continuously circulates.

Two typical dielectric barrier discharge plasma sources and configurations thereof are illustrated as follows:

(1) A Coaxial Dielectric Barrier Discharge Source:

one tungsten rod with a diameter of 0.8 mm is coaxially placed in a quartz tube with an inner diameter of 3 mm, an outer diameter of 5 mm, and a length of 20 cm to serve as a high-voltage electrode, and one layer of copper foil with a length of 15 cm is adhered to the outer wall of the quartz tube to serve as a ground electrode; two ends of the quartz tube are connected to gas pipes, and the airflow of 3 L/min is introduced in the quartz tube during work; the high-voltage power supply adopts a 10 kHz high-voltage sine power supply with the power of 10 W; and plasma is generated in the quartz tube during discharging.

(2) A Surface Type Dielectric Barrier Discharge Source:

a 1 mm-thickness plate copper high-voltage electrode, a 1 mm-thickness aluminum oxide ceramic dielectric plate, and a 0.5 mm-thickness hexagonal mesh stainless steel ground electrode are closely attached to each other, and the discharge area of the mesh ground electrode is 64 cm$^2$; a 2 cm-height closed chamber is arranged below a discharging area of the mesh electrode, pneumatic joints are mounted at the centers of the left and right surfaces of the chamber, and the airflow of 3 L/min flows through the chamber; the high-voltage power supply adopts a 10 kHz high-voltage sine power supply with the power of 10 W; and during discharging, plasma is generated at the contact surface of the mesh opening of the mesh electrode and the dielectric plate.

The above description is merely an overview of the technical solution of the present disclosure. To make the technical means of the present disclosure more comprehensible and implemented by those skilled in the art in accordance with the content of the specification and to make the above and other objectives, features, and advantages of the present disclosure more obvious and understandable, the specific implementations of the present disclosure are illustrated below.

Figure 7:
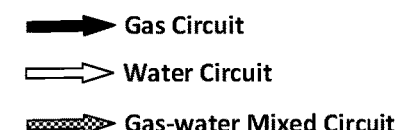
FIG. 7 is a structural schematic diagram of a gliding arc and dielectric barrier discharge combined discharge plasma disinfection device according to the present disclosure.
Figure 7:
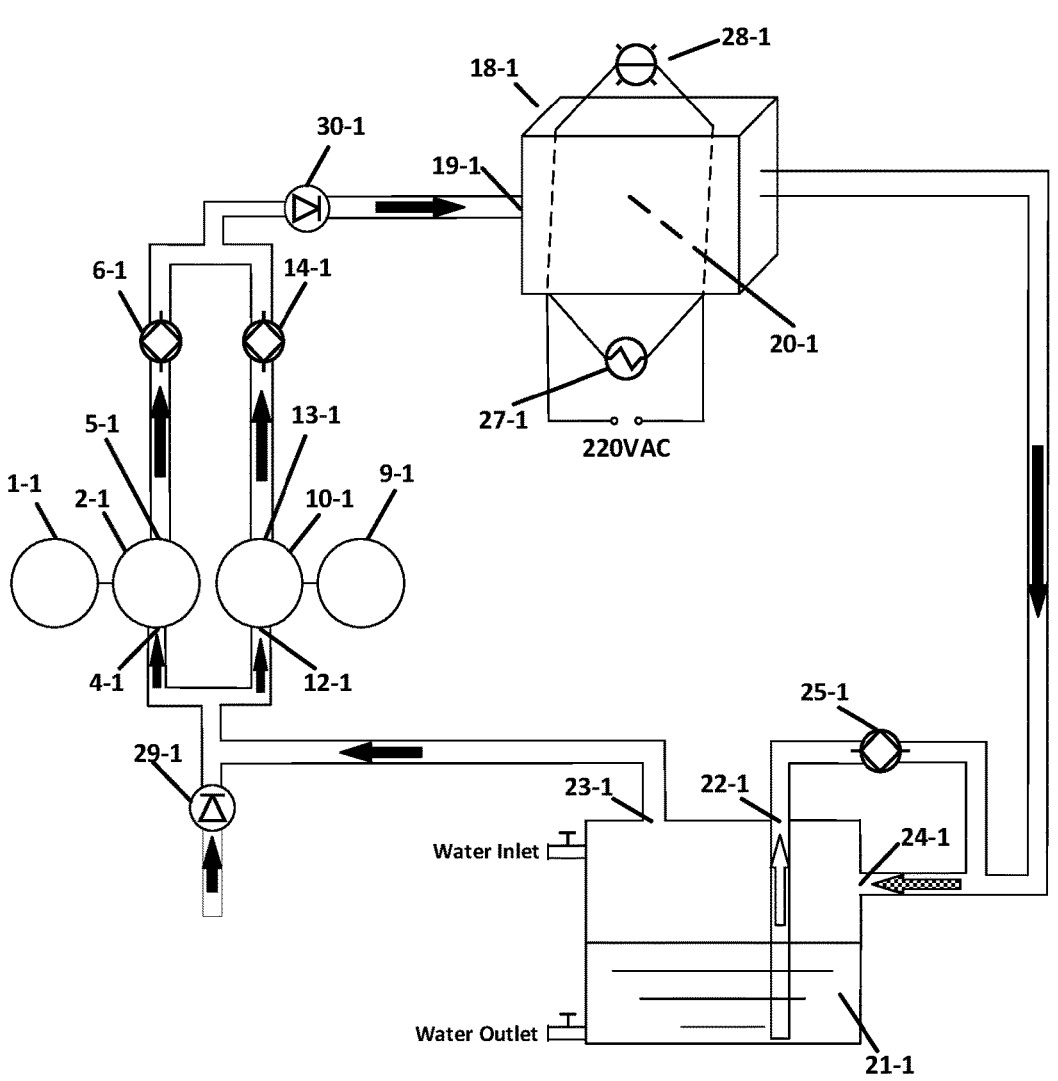
Figure 8:
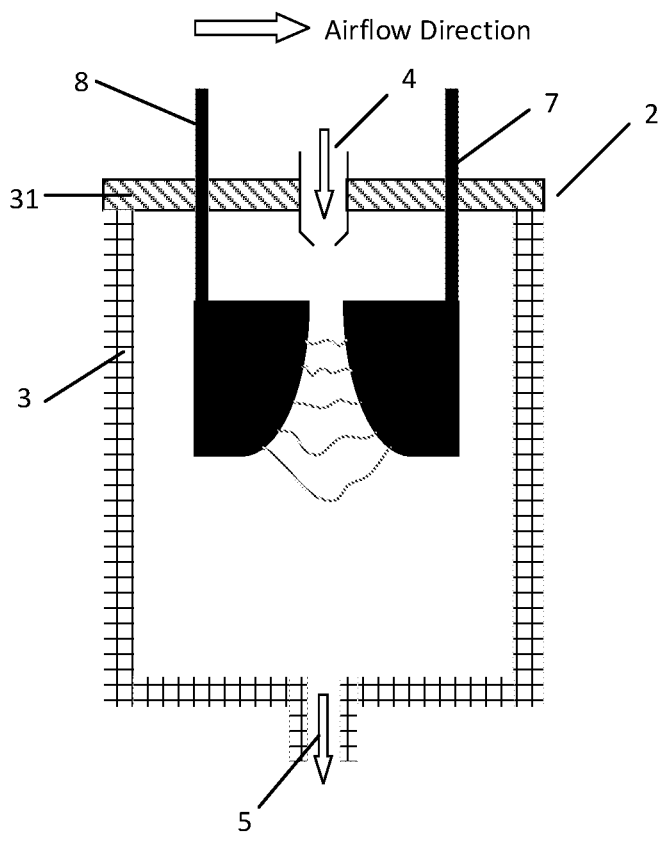
FIG. 8 is a structural schematic diagram of a gliding arc plasma source of a gliding arc and dielectric barrier discharge combined discharge plasma disinfection device according to the present disclosure.
Figure 9:
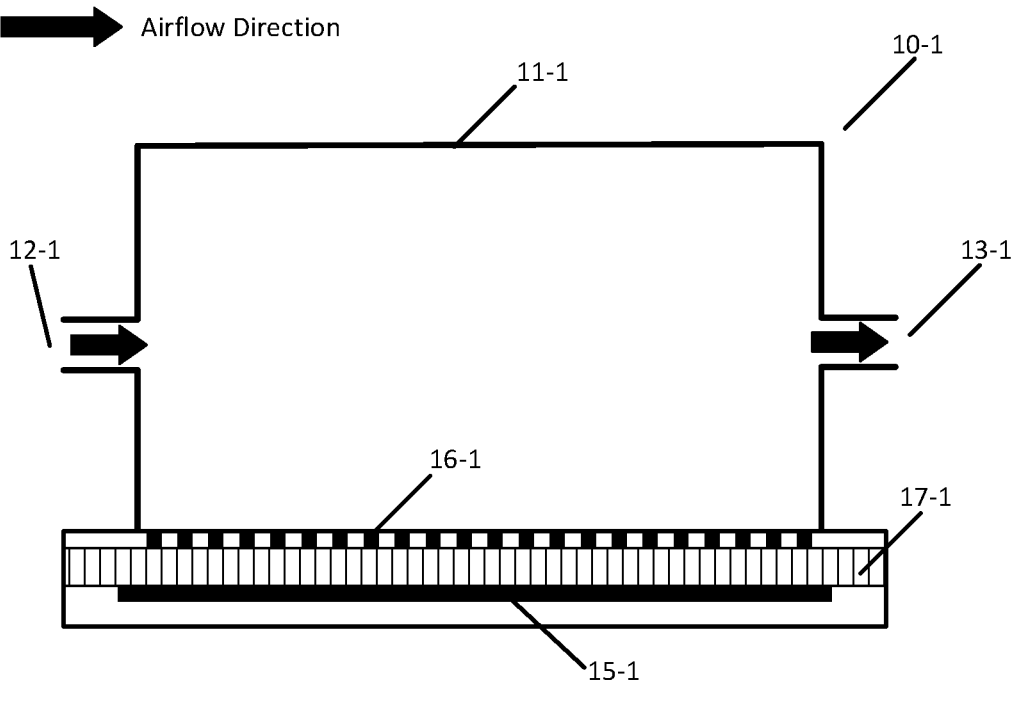
FIG. 9 is a structural schematic diagram of a dielectric barrier discharge plasma source of a gliding arc and dielectric barrier discharge combined discharge plasma disinfection device according to the present disclosure.
Figure 10:
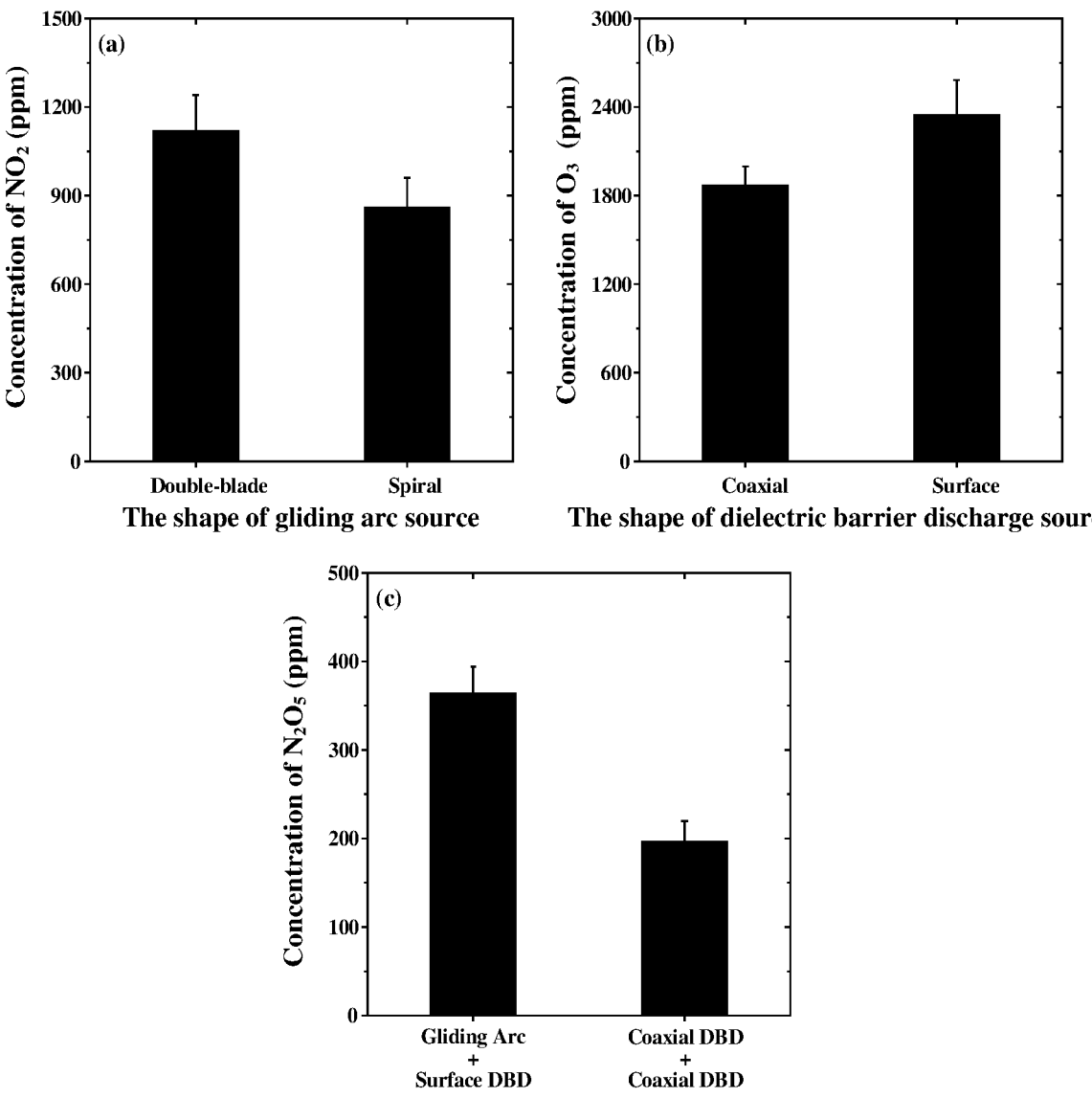
FIG. 10 is a comparison diagram of the yield of nitrogen dioxide ($NO_2$) of the double-blade and spiral gliding arc sources illustrated by the present disclosure under the excitation of a sine high-voltage power supply of 50 Hz and 60 W (a), and a comparison diagram of the yield of ozone ($O_3$) of the coaxial and surface type dielectric barrier discharge sources illustrated by the present disclosure under the excitation of a sine high-voltage power supply of 10 kHz and 10 W (b), and a comparison diagram of the yield of dinitrogen pentoxide ($N_2O_5$) for different combinations of plasma sources under the same power supply and the same mixing parameters (c)

As shown in FIG. 7, a gliding arc and dielectric barrier discharge combined discharge plasma disinfection device includes:

a gliding arc high-voltage power supply 1-1;

as shown in FIG. 8, a gliding arc plasma source 2-1, connected to the gliding arc high-voltage power supply 1-1 and including:

a gliding arc plasma chamber 3-1, provided with a gliding arc gas inlet 4-1 and a gliding arc gas outlet 5-1, wherein the gliding arc gas outlet 5-1 communicates with a gliding arc controllable flow gas pump 6-1, a gliding arc A electrode 7-1, connected to the gliding arc high-voltage power supply 1-1, and a gliding arc B electrode 8-1, connected to the gliding arc high-voltage power supply 1-1, wherein the gliding arc B electrode 8-1 and the gliding arc A electrode 7-1 generate the RNS-dominated reactive gas under the excitation of the gliding arc high-voltage power supply;

a dielectric barrier discharge high-voltage power supply 9-1;

as shown in FIG. 9, a dielectric barrier discharge source 10-1, connected to the dielectric barrier discharge high-voltage power supply 9-1 and including:

a plasma chamber 11-1, provided with a dielectric barrier discharge gas inlet 12-1 and a dielectric barrier discharge gas outlet 13-1, wherein the dielectric barrier discharge gas outlet 13-1 communicates with a dielectric barrier discharge controllable flow gas pump 14-1, a dielectric barrier discharge A electrode 15-1, connected to the dielectric barrier discharge high-voltage power supply 9-1, a dielectric barrier discharge B electrode 16-1, connected to the dielectric barrier discharge high-voltage power supply 9-1, and an insulating dielectric plate 17-1, arranged between the dielectric barrier discharge A electrode 15-1 and the dielectric barrier discharge B electrode 16-1, wherein the dielectric barrier discharge electrode pairs 15-1 and 16-1 generate the ROS-dominated reactive gas under a dielectric barrier discharge voltage, and the ROS-dominated reactive gas; and a reactive gas mixing unit 18-1, including:

an inlet 19-1, connected to the gliding arc controllable flow gas pump 6-1 and the dielectric barrier discharge controllable flow gas pump 14-1, and a reactive gas mixing chamber 20-1, connected to the inlet 19-1 to mix the RNS-dominated reactive gas and the ROS-dominated reactive gas to form the RNS/ROS mixed reactive gas, wherein the dominant product means that it accounts for more than 50% of all the discharge products contained in the reactive gas. The device controls the discharge conditions such as power density and gas temperature of the two plasma sources to enable the dielectric barrier discharge plasma source and the gliding arc plasma source to respectively generate the RNS-dominated reactive gas and the ROS-dominated reactive gas. Under the action of the controllable flow gas pump, the RNS-dominated reactive gas and ROS-dominated reactive gas are mixed in the reactive gas mixing unit 18 in a specific ratio, so that a large number of reactive nitrogen species and reactive oxygen species exist in the RNS/ROS mixed reactive gas at the same time, and a large amount of coexistence state reactive gas with high sterilization effect is generated and enters the reactive gas disinfection unit, thereby realizing sterilization and disinfection in various ways and applications. The RNS/ROS mixed reactive gas may be directly used for disinfection, or may be used to process an aqueous solution and then perform disinfection by using plasma-activated water. The device and the method adopt the ambient air as the raw material, and have the advantages that reactive species have high yield and high permeability and the device has a good sterilization effect and stable property.

In the preferred embodiment of the gliding arc and dielectric barrier discharge combined discharge plasma disinfection device, the disinfection device further includes an activated water disinfection unit which is connected to an outlet of the reactive gas mixing unit 18-1 to import RNS/ROS mixed reactive gas. The activated water disinfection unit includes:

an activated water preparation cavity 21-1, configured to accommodate a solution and provided with a circulating water outlet 22-1, a gas return port 23-1, and a gas-liquid mixture inlet 24-1;

a peristaltic water pump 25-1, one end of which is connected to the outlet of the reactive gas mixing unit 18-1 and the other end is connected to the circulating water outlet 22-1 of the activated water preparation cavity 21-1 to pump the solution to form a gas-liquid mixture and return to the activated water preparation cavity 21-1 through the gas-liquid mixture inlet 24-1; and a gas return channel 26-1, one end of which is connected to the gas return port 23-1, and the other end is connected to the gliding arc gas inlet 4-1 and the dielectric barrier discharge gas inlet 12-1 to circulate gas in the activated water preparation cavity 21-1.

In the preferred embodiment of the gliding arc and dielectric barrier discharge combined discharge plasma disinfection device, the gliding arc high-voltage power supply 1 includes a sine power supply or a direct-current power supply. The gliding arc high-voltage power supply 1-1 has a voltage of more than 5 kV and output power of more than 40 W. The dielectric barrier discharge high-voltage power supply 9-1 has a voltage of more than 5 kV and output power of more than 8 W.

In the preferred embodiment of the gliding arc and dielectric barrier discharge combined discharge plasma disinfection device, the disinfection device further includes a gas injection disinfection unit and/or a gas filling disinfection unit based on the RNS/ROS mixed reactive gas, which is connected to the outlet of the reactive gas mixing unit 18-1.

In the preferred embodiment of the gliding arc and dielectric barrier discharge combined discharge plasma disinfection device, the mixing ratio of the RNS-dominated reactive gas and the ROS-dominated reactive gas entering the reactive gas mixing unit 18-1 is as follows: the volume ratio of the RNS-dominated reactive gas to the ROS-dominated reactive gas is less than or equal to $$\frac{0.328a}{0.556b + 0.051c},$$

wherein a is an absorption value of a Fourier infrared absorption spectrum of the ROS-dominated reactive gas at the position with a wave-number of 1055 $cm^{-1}$, b is an absorption value of a Fourier infrared absorption spectrum of the RNS-dominated reactive gas at the position of a wave-number of 1630 $cm^{-1}$, and c is an absorption value of a Fourier infrared absorption spectrum of the RNS-dominated reactive gas at the position of a wave-number of 1900 $cm^{-1}$.

In the preferred embodiment of the gliding arc and dielectric barrier discharge combined discharge plasma disinfection device, the reactive gas mixing chamber 20-1 further includes:

a heater 27-1, configured to heat the RNS/ROS mixed reactive gas in the reactive gas mixing chamber 20-1 and control the temperature of the reactive gas mixing chamber 20-1 to be 30-50 DEG C. to accelerate the thermal motion of molecules and prevent the decomposition of reactive oxygen species at higher temperature, so that the RNS-dominated reactive gas generated by gliding arc discharge and the ROS-dominated reactive gas generated by dielectric barrier discharge are fully mixed; and an ultraviolet lamp 28-1, configured to irradiate the RNS/ROS mixed reactive gas and enhance the reaction degree of the RNS/ROS mixed reactive gas, wherein ultraviolet light decomposes oxygen molecules in the air to generate free oxygen atoms, that is, reactive oxygen species, thereby further preventing decomposition of the reactive oxygen species and accelerating the mixing rate of the RNS-dominated reactive gas and ROS-dominated reactive gas.

In the preferred embodiment of the gliding arc and dielectric barrier discharge combined discharge plasma disinfection device, the gliding arc gas inlet and the dielectric barrier discharge gas inlet are connected to a gas supplementing valve 29-1, the gas supplementing valve 29-1 is a one-way valve without an opening gas pressure, and the outlet of the gas supplementing valve 29-1 is connected to the gliding arc gas inlet 4-1 and the dielectric barrier discharge gas inlet 12-1.

In the preferred embodiment of the gliding arc and dielectric barrier discharge combined discharge plasma disinfection device, the gliding arc controllable flow gas pump 6-1 and the dielectric barrier discharge controllable flow gas pump 14-1 are connected to the inlet 19-1 through a check one-way valve 30-1.

In the preferred embodiment of the gliding arc and dielectric barrier discharge combined discharge plasma disinfection device, the gliding arc plasma source 2-1 includes a sealing end 31-1 sealing the gliding arc plasma chamber 3-1.

In one embodiment, the device includes a gliding arc plasma source 2-1, a dielectric barrier discharge plasma source 10-1, a reactive gas mixing unit 18, and a reactive gas disinfection unit. The gliding arc plasma source is configured to discharge under the excitation of the gliding arc high-voltage power supply and generate the RNS-dominated reactive gas. The gliding arc high-voltage power supply, serving as a discharge power supply of the gliding arc plasma source, may generate a high-voltage power supply of 5 kV or above, may provide an output power of more than 40 W, and may resist voltage fluctuation caused by the temperature change of the gliding arc plasma source. The gliding arc high-voltage power supply may select a sine power supply or a direct-current power supply.

The dielectric barrier discharge plasma source is configured to discharge under the excitation of the dielectric barrier discharge high-voltage power supply and generate the ROS-dominated reactive gas. The dielectric barrier discharge high-voltage power supply, serving as a discharge power supply of the dielectric barrier discharge plasma source, may generate a high-voltage power supply of 5 kV or above, may provide an output power of more than 8 W, and may resist voltage fluctuation caused by the temperature change of the dielectric barrier discharge plasma source.

The reactive gas mixing chamber 20-1 is configured to contain RNS-dominated reactive gas and ROS-dominated reactive gas from two plasma sources and serve as a reaction chamber of the two reactive gases.

The reactive gas disinfection unit may be directly used for direct sterilization and disinfection by gas, or may be configured to process an aqueous solution to obtain plasma-activated water for indirect sterilization and disinfection.

When direct sterilization and disinfection are performed by gas, the implementation of the reactive gas disinfection unit includes, but is not limited to: a wet surface is disinfected by a method for injecting the RNS/ROS mixed reactive gas, and objects in the space are disinfected or kept fresh by a method for filling the closed space with the RNS/ROS mixed reactive gas.

When the aqueous solution is processed to obtain the plasma-activated water for indirect sterilization and disinfection, the aqueous solution such as tap water, ultrapure water, deionized water, medical normal saline, or diluted $H_2O_2$ solution may be activated. The implementation of the sterilization and disinfection by the activated water includes, but is not limited to: sterilization or disinfection is performed by washing, spraying, and soaking.

The disinfection device controls the voltage and power of the two plasma sources to enable the gliding arc and dielectric barrier discharge plasma generating units to respectively generate the RNS-dominated reactive gas and the ROS-dominated reactive gas. Under the action of the controllable flow gas pump, the RNS-dominated reactive gas and ROS-dominated reactive gas are mixed in the reactive gas mixing unit 18-1 in a specific ratio and enter the reactive gas disinfection unit to realize sterilization and disinfection in various ways and applications.

A method for a gliding arc and dielectric barrier discharge combined discharge plasma disinfection device includes the following steps:

a gliding arc high-voltage power supply 1-1 provides a discharge voltage of a gliding arc plasma source 2-1, a gliding arc plasma source 2-1 generates the RNS-dominated reactive gas, a dielectric barrier discharge high-voltage power supply 9-1 provides a discharge voltage of a dielectric barrier discharge plasma source 10-1, and a dielectric barrier discharge plasma source 10-1 generates the ROS-dominated reactive gas;

a gliding arc gas outlet 5-1 exports a predetermined amount of RNS-dominated reactive gas by a gliding arc controllable flow gas pump 6-1, a dielectric barrier discharge gas outlet 13-1 exports a predetermined amount of ROS-dominated reactive gas by a dielectric barrier discharge controllable flow gas pump 14-1, and a reactive gas mixing chamber 20-1 mixes the RNS-dominated reactive gas and the ROS-dominated reactive gas according to a mixing ratio to form the RNS/ROS mixed reactive gas, wherein the volume ratio of the RNS-dominated reactive gas to the ROS-dominated reactive gas is less than or equal to $$\frac{0.328a}{0.556b + 0.051c},$$

a being an absorption value of a Fourier infrared absorption spectrum of the ROS-dominated reactive gas at the position with a wave-number of 1055 cm$^{-1}$, b being an absorption value of a Fourier infrared absorption spectrum of the RNS-dominated reactive gas at the position of a wave-number of 1630 cm$^{-1}$, and c being an absorption value of a Fourier infrared absorption spectrum of the RNS-dominated reactive gas at the position of a wave-number of 1900 cm$^{-1}$.

The RNS/ROS mixed reactive gas is imported into an activated water disinfection unit and/or a gas injection disinfection unit and/or a gas filling disinfection unit through an outlet of a reactive gas mixing unit 18-1.

The RNS/ROS mixed reactive gas enters the reactive gas disinfection unit to perform disinfection through gas injection and gas filling, or performs disinfection by washing, soaking, and spraying after plasma-activated water is prepared.

Example 1

The structure of the example is shown in FIG. 7.

In this example, a double-blade gliding arc source and a surface type dielectric barrier discharge source are selected, wherein the structure of the gliding arc plasma source is shown in FIG. 8: an inner cavity is 60 mm in length, 10 mm in width, and 90 mm in height, a quartz chamber has a wall thickness of 5 mm, gas pipes are connected to openings of upper and lower surfaces, two stainless steel knife-shaped electrodes are fixed inside, one serves as a high-voltage electrode and the other one serves as a low-voltage electrode, the stainless steel electrodes are 3 mm in thickness, the narrowest part of the two electrodes is 2 mm and the widest part is 20 mm, and plasma is generated between the two knife-shaped electrodes during discharging. The structure of the dielectric barrier discharge plasma source is shown in FIG. 9: a 1 mm-thickness plate copper high-voltage electrode, a 1 mm-thickness aluminum oxide ceramic dielectric plate and a 0.5 mm-thickness hexagonal mesh stainless steel ground electrode are closely attached to each other, and the discharge area of the mesh ground electrode is 64 cm$^2$; a 2 cm-height closed chamber is arranged below a discharging area of mesh electrode, pneumatic joints are mounted at the centers of the left and right surfaces of the chamber, and the power is 10 W; and during discharging, plasma is generated at the contact surface of the mesh opening of the mesh electrode and the dielectric plate. A high-voltage sine power supply of 15 kV and 50 Hz is applied to the gliding arc plasma source, and the discharging power is 60 W so that the gliding arc plasma source generates the RNS-dominated reactive gas. A high-voltage sine power supply of 7 kV and 10 kHz is applied to the dielectric barrier discharge plasma source, and the discharging power is 10 W so that the dielectric barrier discharge plasma source generates the ROS-dominated reactive gas. The controllable flow gas pumps 1 and 2 control the flow rate of gas passing through the plasma source to be 1 SLM and 3 SLM respectively. Under the action of the controllable flow gas pumps, RNS-dominated reactive gas and ROS-dominated reactive gas enter the reactive gas mixing unit 18 through the check one-way valve 30 for mixing and reaction, and are mixed dramatically and completely under the action of the gas heater 27 and the ultraviolet lamp 28. The aqueous solution in the activated water preparation cavity 21 completely reacts with the RNS/ROS mixed reactive gas under the pumping of the peristaltic water pump 25 to improve the solubility of the reactive species in the aqueous solution, and the aqueous solution is set as 50 mL. The tail gas after the reaction is dried and then reenters the gas inlet end of the plasma source through the gas circuit for recycling. The discharge working time is set as 10 minutes. The prepared plasma-activated water may be configured to disinfect various occasions. It may be seen from the comparison of FIG. 3 that the disinfection performance of the present disclosure is obviously improved.

In this embodiment, the aqueous solution is any one of tap water, ultrapure water, deionized water, normal saline, or diluted hydrogen peroxide solution.

In this embodiment, the high-voltage power supply is any one of pulse and sine high-voltage power supplies.

Bacterial Detection:

1. a bacterial number detection culture medium: a plate count agar (PCA) (TSB culture medium) was sterilized at 121 DEG C. for 15 minutes, and finally the pH value was 7.0±0.2 (15 ml/plate).

The original bacteria of the tested bacteria adopt the original bacterial solution of methicillin-resistant *Staphylococcus aureus* (MRSA) of absorbance of OD600=2.

Phosphate buffer diluent is a freshly prepared sterile PBS aqueous solution with PH 7.2, which is handled according to the bacterial number test method of the food microorganism test method, FDA Taiwan (reference: bacterial number test method of the food microorganism test method, FDA Taiwan; https://www.fda.gov.tw/upload/133/Content).

2. Bacterial number detection sterilization effect treatment: 0.1 mL of the original bacterial solution was added into 0.9 mL of the processed aqueous solution for uniformly mixing and reaction for 5 minutes. A sterilized straw absorbed 0.1 mL of the above mixed liquid and added it in 0.9 mL of diluent, and a series of dilution test liquids of 10-1,000,000 were prepared in sequence. Finally, 10 uL of each of the dilution test liquids was absorbed by a drip plate technology method and was dropped into the culture medium respectively, and each of the test liquids was subjected to the operation for three times repeatedly. 10 uL of bacterial original liquid diluent of 10-1,000,000 was dropped in the culture medium as a blank control group (repeated for three times).

3. A bacterial colony culture test: the above culture medium plate was stood and then was inverted at 37±0.5° C. for culture for 48±2 hours after the bacterial diluent was dried.

Result and Discussion:

The above plasma source is used, and when the airflow of the gliding arc plasma source is 1 SLM and the airflow of the dielectric barrier discharge plasma source is 3 SLM, it is the ideal mixed form, that is, the reactive nitrogen species and the reactive oxygen species may be mixed completely and coexist.

Figure 11:
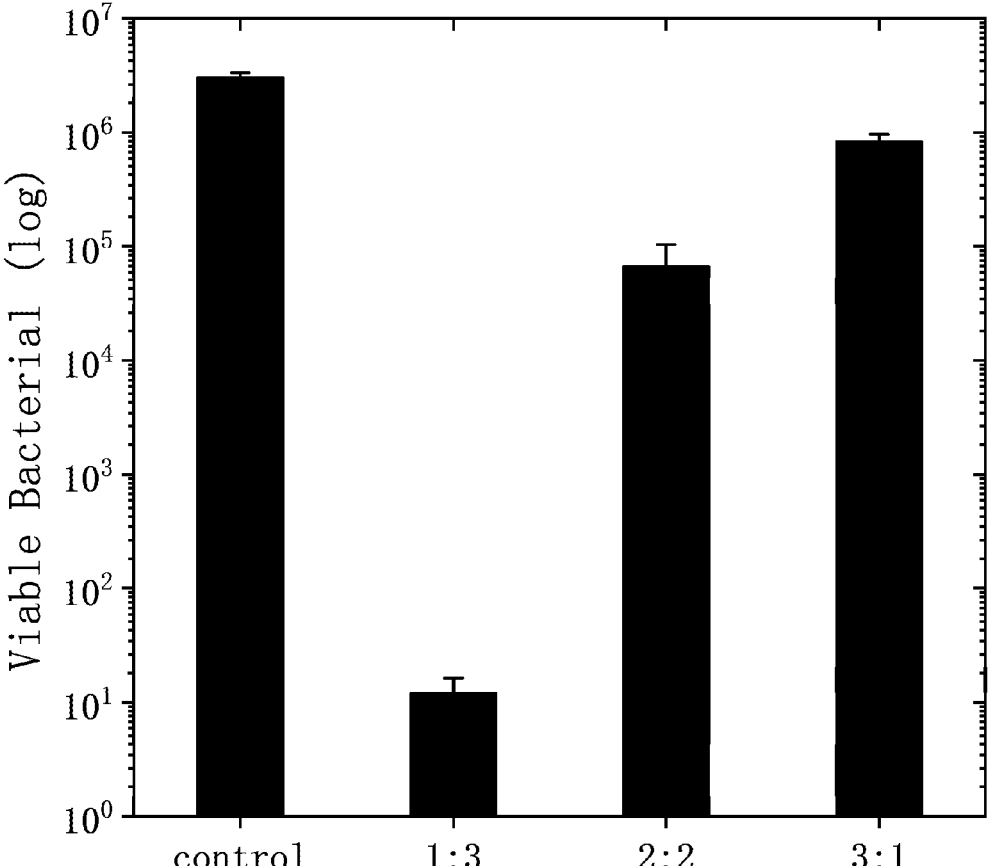
FIG. 11 is a comparison diagram of the gliding arc and dielectric barrier discharge combined sterilization effect according to an embodiment of the present disclosure so as to realize the coexistence of the reactive oxygen species and the reactive nitrogen species in an ideal mixing ratio that meets the condition that the volume ratio of RNS-dominated reactive gas to the ROS-dominated reactive gas is less than or equal to $$\frac{0.328a}{0.556b + 0.051c}$$

As shown in FIG. 11, 1:3, 2:2, and 3:1 refer to the mixing ratio of the RNS-dominated reactive gas to the ROS-dominated reactive gas, the sterilization effect is the best when the flow speed ratio of the gliding arc discharge to the dielectric barrier discharge is 1:3, and the sterilization effect may reach more than 6 orders of magnitude compared with the control group; when the flow speed ratio is 2:2, the sterilization effect only has 2 orders of magnitude; and when the flow speed ratio is 3:1, the sterilization effect only has 1 order of magnitude.

The processing sequence of the gliding arc discharge and the dielectric barrier discharge is changed, the mixed mode has the best effect when the flow speed is 1-3, and the sterilization effect may reach more than 6 orders of magnitude compared with the control group; if the RNS-dominated reactive gas of 1 SLM is introduced for 10 minutes and then the ROS-dominated reactive gas of 3 SLM is introduced for 10 minutes, the sterilization effect has only 2 orders of magnitude; and if the ROS-dominated reactive gas of 3 SLM is introduced for 10 minutes and then the RNS-dominated reactive gas of 1 SLM is introduced for 10 minutes, no sterilization effect is achieved.

After the aqueous solution treated by the ideal mixing when the flow speed ratio is 1-3 is stood, the sterilization effect decreases with time, and the sterilization effect is completely lost after 120 minutes.

Compared with the control group, the sterilization effect using the internal recycle system may reach more than 6 orders of magnitude, and the sterilization effect not using the internal recycle system may reach 4 orders of magnitude, so using the internal recycle system may increase the sterilization effect by more than 2 orders of magnitude.

Although the embodiments of the present disclosure are described above with reference to the drawings, the present disclosure is not limited to the above specific embodiments and application fields, and the above specific embodiments are merely illustrative, instructive, rather than restrictive. Those of ordinary skills in the art can make various forms under the inspiration of this specification and without departing from the protection scope of the claims of the present disclosure, and these forms are all within the protection scope of the present disclosure.

The invention claimed is:

1. A discharge plasma disinfection device, comprising:
a first high-voltage power, configured to provide a first voltage;
a first plasma source, connected to the first high-voltage power supply, the first plasma source comprising;
a first plasma chamber, provided with a first air inlet and a first air outlet, the first air outlet communicating with a first controllable flow gas pump;
a first A electrode, connected to the first high-voltage power supply; and
a first B electrode, parallel to the first A electrode and connected to the first high-voltage power supply;
wherein the first A electrode and the first B electrode generate a first plasma gas in the first plasma chamber under a first voltage, and the first plasma gas is dominated by nitrogen oxides;
a second high-voltage power, configured to provide a second voltage;
a second plasma source, connected to the second high-voltage power supply, the second plasma source comprising;
a second plasma chamber, provided with a second air inlet and a second air outlet, the second air outlet communicating with a second controllable flow gas pump;
a second A electrode, connected to the second high-voltage power supply;
a second B electrode, parallel to the second A electrode and connected to the second high-voltage power supply;
an insulating dielectric plate, set between the second A electrode and the second B electrode;
the second A electrode and the second B electrode generate a second plasma gas in the second plasma chamber under a second voltage, and the second plasma gas is dominated by ozone;
a reactive gas mixing unit, comprising;
an inlet, connected to a first controllable flow air pump and the second controllable flow air pump; and
a reactive gas mixing chamber, connected to the inlet to mix the first plasma gas and the second plasma gas to form the mixed reactive gas, wherein the reactive gas mixing unit is configured to mix the first plasma gas and the second plasma gas to form a mixed reactive gas;
a supplementary valve, wherein the first air inlet and the second air inlet are connected to the supplementary valve, and the supplementary valve is a one-way valve without an opening air pressure; and an outlet of the gas supplementing valve is connected to the gas inlet of the gliding arc plasma source and the gas inlet of the dielectric barrier discharge plasma source;
a check one-way valve, wherein the first controllable flow air pump and the second controllable flow air pump are connected to the inlet via the check one-way valve;
an activated water disinfection and sterilization unit, which is connected to the outlet of the reactive gas mixing unit to introduce mixed reactive gas; the activated water disinfection and sterilization unit includes,
an activated water preparation chamber, which contains the solution and is provided with a circulating water outlet, a gas return port and a gas-liquid mixture inlet,
a peristaltic water pump, which has one end connected to the outlet of the reactive gas mixing unit, and the other end connected to the circulating water outlet of the activated water preparation chamber to pump the solution to form a gas-liquid mixture, and return to the activated water preparation chamber through the gas-liquid mixture inlet;

an air return passage, one end of which is connected to the air gas return port and the other end is connected to the first air inlet and the second air inlet to circulate activated water to prepare the gas in the cavity; wherein the first A electrode and the first B electrode are used for generating a first plasma gas under a first voltage, wherein the first plasma gas is mainly produced by nitrogen oxide and the nitrogen oxide accounts for more than 90% of the total plasma discharge products;

the second A electrode and the second B electrode are used for generating a second plasma gas under a second voltage, wherein the second plasma gas is mainly produced by ozone and the ozone accounts for more than 80% of the total products of the plasma discharge; and the mixed reactive gas can be directly used for disinfection and sterilization, or the aqueous solution is processed first, and then the plasma-activated water is used for disinfection and sterilization; and the voltage of the first high-voltage power supply is more than 10 kV and the output power is more than 200 W, and the voltage of the second high-voltage power supply is more than 5 kV and the output power is more than 8 W.

2. The disinfection device according to claim 1, wherein the first plasma gas and the second plasma gas are mixed as follows:

the volume of the ozone reactive gas: the volume of the nitrogen oxide reactive gas $$\geq \frac{0.556b + 0.051c}{0.328a},$$

wherein a is an absorption value of a Fourier infrared absorption spectrum of the second plasma gas at the position with a wave-number of 1055 cm$^{-1}$, b being an absorption value of a Fourier infrared absorption spectrum of the first plasma gas at the position of a wave-number of 1630 cm$^{-1}$, and c being an absorption value of a Fourier infrared absorption spectrum of the first plasma gas at the position of a wave-number of 1900 cm$^{-1}$.

3. The disinfection device according to claim 1, wherein the disinfection device further comprises a gas spray disinfection unit and/or a gas filling disinfection unit based on the mixed reactive gas, both of which are connected to the outlet of the reactive gas mixing unit.

4. A discharge plasma disinfection device, comprising:
a gliding arc high-voltage power supply;
a gliding arc plasma source, comprising:
a gliding arc electrode pair including a gliding arc A electrode, connected to the gliding arc high-voltage power supply, and a gliding arc B electrode, parallel to the a gliding arc A electrode and connected to the gliding arc high-voltage power supply, wherein the gliding arc electrode pair is configured to generate the reactive nitrogen species (RNS)-dominated reactive gas under the excitation of a gliding arc high-voltage power supply; connected to the gliding arc high-voltage power supply and generating the RNS-dominated reactive gas under the excitation of the gliding arc high-voltage power supply;

a gliding arc controllable flow gas pump;
a dielectric barrier discharge high-voltage power supply;
a dielectric barrier discharge plasma source, comprising:
a dielectric barrier discharge electrode pair including a dielectric barrier discharge A electrode and a dielectric barrier discharge B electrode parallel to dielectric barrier discharge A electrode, configured to generate the reactive oxygen species (ROS)-dominated reactive gas under the excitation of a dielectric barrier discharge high-voltage power supply; connected to the dielectric barrier discharge high-voltage power supply and generating the ROS-dominated reactive gas under the excitation of the dielectric barrier discharge high-voltage power supply;

an insulating dielectric plate, arranged between the dielectric barrier discharge A electrode and the dielectric barrier discharge B electrode;

a dielectric barrier discharge controllable flow gas pump;
a reactive gas mixing unit, comprising:
an inlet, connected to a gliding arc controllable flow gas pump and the dielectric barrier discharge controllable flow gas pump;

a reactive gas mixing chamber, connected to the inlet to mix the RNS-dominated reactive gas and the ROS-dominated reactive gas to form the RNS/ROS mixed reactive gas; and a supplementary valve, wherein the first air inlet and the second air inlet are connected to the supplementary valve, and the supplementary valve is a one-way valve without an opening gas pressure;

a check one-way valve, wherein the gliding arc controllable flow gas pump and the dielectric barrier discharge controllable flow gas pump are connected to the inlet via the check one-way valve;

an internal recycle system unit, configured to reconnect the unused RNS/ROS mixed reactive gas to a gas input end of the gliding arc electrode pair and a gas input end of the dielectric barrier discharge electrode pair; and a heater, configured to heat the RNS/ROS mixed reactive gas in a reactive gas mixing chamber and control the temperature of the reactive gas mixing chamber to be 30-50 DEG C.; and an ultraviolet lamp, configured to irradiate the RNS/ROS mixed reactive gas;

wherein the RNS/ROS mixed reactive gas is directly configured to perform disinfection, or is configured to process an aqueous solution and then perform disinfection by using plasma-activated water; and the gliding arc high-voltage power supply comprises a sine power supply or a direct-current power supply, the gliding arc high-voltage power supply has a voltage of more than 5 kV and output power of more than 40 W, and the dielectric barrier discharge high-voltage power supply has a voltage of more than 5 kV and output power of more than 8 W.

5. The disinfection device according to claim 4, further comprising a gas injection disinfection unit and/or a gas filling disinfection unit based on the RNS/ROS mixed reactive gas, which is connected to an outlet of the reactive gas mixing unit.

6. The disinfection device according to claim 4, wherein the mixing ratio of the RNS-dominated reactive gas and the ROS-dominated reactive gas entering the reactive gas mixing unit is as follows:

the volume ratio of the RNS-dominated reactive gas to the ROS-dominated reactive gas is less than or equal to $$\frac{0.328a}{0.556b + 0.051c},$$ 5 a being an absorption value of a Fourier infrared absorption spectrum of the ROS-dominated reactive gas at the position with a wave-number of 1055 cm$^{-1}$, 10 b being an absorption value of a Fourier infrared absorption spectrum of the RNS-dominated reactive gas at the position of a wave-number of 1630 cm$^{-1}$, and c being an absorption value of a Fourier infrared absorption spectrum of the RNS-dominated reactive 15 gas at the position of a wave-number of 1900 cm$^{-1}$.

\* \* \* \* \*